United States Patent
Watt et al.

(10) Patent No.: US 10,703,786 B2
(45) Date of Patent: Jul. 7, 2020

(54) METHODS AND COMPOSITIONS FOR IMPROVING GLUCOSE METABOLISM

(71) Applicant: MONASH UNIVERSITY, Clayton, Victoria (AU)

(72) Inventors: Matthew Watt, Lysterfield (AU); Ruth Meex, Cheltenham (AU)

(73) Assignee: THE UNIVERSITY OF MELBOURNE, Victoria (AU)

( * ) Notice: Subject to any disclaimer, the term of this patent is extended or adjusted under 35 U.S.C. 154(b) by 0 days.

(21) Appl. No.: 15/771,980

(22) PCT Filed: Oct. 28, 2016

(86) PCT No.: PCT/AU2016/051020
§ 371 (c)(1),
(2) Date: Apr. 27, 2018

(87) PCT Pub. No.: WO2017/070744
PCT Pub. Date: May 4, 2017

(65) Prior Publication Data
US 2018/0362602 A1    Dec. 20, 2018

(30) Foreign Application Priority Data
Oct. 30, 2015  (AU) ............... 2015904460

(51) Int. Cl.
C07K 14/47    (2006.01)
A61K 38/17    (2006.01)
C07K 16/46    (2006.01)
A61P 3/10     (2006.01)

(52) U.S. Cl.
CPC ...... *C07K 14/4702* (2013.01); *A61K 38/1709* (2013.01); *A61P 3/10* (2018.01); *C07K 16/46* (2013.01); *C07K 2319/30* (2013.01)

(58) Field of Classification Search
CPC .... C07K 14/47; C07K 14/4702; C07K 16/46; A61P 3/10
See application file for complete search history.

(56) References Cited

U.S. PATENT DOCUMENTS 9,061,059 B2    6/2015   Chakraborty et al.
2011/0256100 A1  10/2011  Thomas et al.
2013/0067608 A1  3/2013   Domon et al.
2014/0193373 A1  7/2014   Ku
2014/0329704 A1  11/2014  Melton et al.
2015/0050728 A1  2/2015   Benvenisty et al.

FOREIGN PATENT DOCUMENTS

WO    WO 2002/002771 A2    1/2002
WO    2011/107586 A1       9/2011
WO    2013/012781 A1       1/2013
WO    WO 2014/014819 A2    1/2014

OTHER PUBLICATIONS

Vannahme, C., et al.; Characterization of SMOC-1, a Novel Modular Calcium-binding Protein in Basement Membranes; Jour. of Biol. Chem.(2002), vol. 277, No. 41; pp. 37977-37986.

Vannahme, C., et al.; Characterization of SMOC-2, a modular extracellular calcium-binding protein; Biochem. J. (2003), vol. 373, pp. 805-814.

Australian Patent Office—International Search Report; PCT/AU2016/051020; dated Dec. 20, 2016.

European Patent Office; Supplementary European Search Report; Application No. EP 16858508; dated Mar. 26, 2019.

Montgomery, et al; SMOC1—A new therapeutic target for glycaemic control?; Oral Presentation—ASN Events; Aug. 30, 2017.

Choi, et al; SMOC1-induced osteoblast differentiation involves proliferation of human bone marrow mesenchymal stem cells; Tissue Engineering and Regenerative Medicine; Mar. 2014; 11:304-316.

Zhang, et al; Multistage genome-wide association meta-analyses identified two new loci for bone mineral density; Human Molecular Genetics; Nov. 2013; 23:7:1-11.

Zhong, et al; Temporal Profiling of the Secretome during Adipogenesis in Humans; Journal of Proteome Research; May 2010; 9:5228-5238.

*Primary Examiner* — Karen Cochrane Carlson
(74) *Attorney, Agent, or Firm* — Kilpatrick Townsend & Stockton LLP

(57) ABSTRACT

The present invention relates to compositions, methods and kits for promoting glucose clearance in an individual. In particular, the compositions, methods and kits are particularly useful, but not limited to, the treatment of insulin resistance or type 2 diabetes. The invention provides a method of promoting blood glucose clearance in an individual, the method comprising administering SMOC1 to the individual. Preferably, the individual has an impaired ability to clear glucose from the blood. Typically, the individual displays a level of insulin resistance.

23 Claims, 7 Drawing Sheets

Specification includes a Sequence Listing.

A.

B.

SEQUENCE LISTING

<160> NUMBER OF SEQ ID NOS: 4

<210> SEQ ID NO 1
<211> LENGTH: 435
<212> TYPE: PRT
<213> ORGANISM: Homo sapiens

<400> SEQUENCE: 1

Met Leu Pro Ala Arg Cys Ala Arg Leu Leu Thr Pro His Leu Leu Leu
1               5                   10                  15

Val Leu Val Gln Leu Ser Pro Ala Arg Gly His Arg Thr Thr Gly Pro
            20                  25                  30

Arg Phe Leu Ile Ser Asp Arg Asp Pro Gln Cys Asn Leu His Cys Ser
        35                  40                  45

Arg Thr Gln Pro Lys Pro Ile Cys Ala Ser Asp Gly Arg Ser Tyr Glu
    50                  55                  60

Ser Met Cys Glu Tyr Gln Arg Ala Lys Cys Arg Asp Pro Thr Leu Gly
65                  70                  75                  80

Val Val His Arg Gly Arg Cys Lys Asp Ala Gly Gln Ser Lys Cys Arg
                85                  90                  95

Leu Glu Arg Ala Gln Ala Leu Glu Gln Ala Lys Lys Pro Gln Glu Ala
            100                 105                 110

Val Phe Val Pro Glu Cys Gly Glu Asp Gly Ser Phe Thr Gln Val Gln
        115                 120                 125

Cys His Thr Tyr Thr Gly Tyr Cys Trp Cys Val Thr Pro Asp Gly Lys
    130                 135                 140

Pro Ile Ser Gly Ser Ser Val Gln Asn Lys Thr Pro Val Cys Ser Gly
145                 150                 155                 160

Ser Val Thr Asp Lys Pro Leu Ser Gln Gly Asn Ser Gly Arg Lys Asp
                165                 170                 175

Asp Gly Ser Lys Pro Thr Pro Thr Met Glu Thr Gln Pro Val Phe Asp
            180                 185                 190

Gly Asp Glu Ile Thr Ala Pro Thr Leu Trp Ile Lys His Leu Val Ile
        195                 200                 205

Lys Asp Ser Lys Leu Asn Asn Thr Asn Ile Arg Asn Ser Glu Lys Val
    210                 215                 220

```
Tyr Ser Cys Asp Gln Glu Arg Gln Ser Ala Leu Glu Glu Ala Gln Gln
225                 230                 235                 240

Asn Pro Arg Glu Gly Ile Val Ile Pro Glu Cys Ala Pro Gly Gly Leu
            245                 250                 255

Tyr Lys Pro Val Gln Cys His Gln Ser Thr Gly Tyr Cys Trp Cys Val
        260                 265                 270

Leu Val Asp Thr Gly Arg Pro Leu Pro Gly Thr Ser Thr Arg Tyr Val
    275                 280                 285

Met Pro Ser Cys Glu Ser Asp Ala Arg Ala Lys Thr Thr Glu Ala Asp
290                 295                 300

Asp Pro Phe Lys Asp Arg Glu Leu Pro Gly Cys Pro Glu Gly Lys Lys
305                 310                 315                 320

Met Glu Phe Ile Thr Ser Leu Leu Asp Ala Leu Thr Thr Asp Met Val
            325                 330                 335

Gln Ala Ile Asn Ser Ala Ala Pro Thr Gly Gly Gly Arg Phe Ser Glu
        340                 345                 350

Pro Asp Pro Ser His Thr Leu Glu Glu Arg Val Val His Trp Tyr Phe
    355                 360                 365

Ser Gln Leu Asp Ser Asn Ser Ser Asn Asp Ile Asn Lys Arg Glu Met
370                 375                 380

Lys Pro Phe Lys Arg Tyr Val Lys Lys Ala Lys Pro Lys Lys Cys
385                 390                 395                 400

Ala Arg Arg Phe Thr Asp Tyr Cys Asp Leu Asn Lys Asp Lys Val Ile
            405                 410                 415

Ser Leu Pro Glu Leu Lys Gly Cys Leu Gly Val Ser Lys Glu Val Gly
        420                 425                 430

Arg Leu Val
        435

<210> SEQ ID NO 2
<211> LENGTH: 1308
<212> TYPE: DNA
<213> ORGANISM: Homo sapiens

<400> SEQUENCE: 2
atgctgcccg cgcgctgcgc ccgcctgctc acgccccact tgctgctggt gttggtgcag     60
ctgtcccctg ctcgcggcca ccgcaccaca ggccccaggt ttctaataag tgaccgtgac    120
ccacaatgca acctccactg ctccaggact caacccaaac ccatctgtgc ctctgatggc    180
aggtcctacg agtccatgtg tgagtaccag cgagccaagt gccgagaccc gaccctgggc    240
gtggtgcatc gaggtagatg caaagatgct ggccagagca agtgtcgcct ggagcgggct    300
caagccctgg agcaagccaa gaagcctcag gaagctgtgt tgtcccgaga gtgtggcgag    360
gatggctcct ttacccaggt gcagtgccat acttacactg gtactgctgg tgtgtcacc     420 ccggatggga agcccatcag tggctcttct gtgcagaata aaactcctgt atgttcaggt    480
tcagtcaccg acaagccctt gagccagggt aactcaggaa ggaaagatga cgggtctaag    540
ccgacaccca cgatggagac ccagccggtg ttcgatggag atgaaatcac agccccaact    600
ctatggatta acacttggt gatcaaggac tccaaactga caacaccaa cataagaaat    660 tcagagaaag tctattcgtg tgaccaggag aggcagagtg ctctggaaga ggcccagcag    720
aatccccgtg agggtattgt catccctgaa tgtgcccctg ggggactcta taagccagtg    780
caatgccacc agtccactgg ctactgctgg tgtgtgctgg tggacacagg cgcccgctg    840
```

-continued

```
cctgggacct ccacacgcta cgtgatgccc agttgtgaga gcgacgccag ggccaagact    900
acagaggcgg atgacccctt caaggacagg gagctaccag gctgtccaga agggaagaaa    960
atggagttta tcaccagcct actggatgct ctcaccactg acatggttca ggccattaac   1020
tcagcagcgc ccactggagg tgggaggttc tcagagccag accccagcca cccctggag    1080 gagcgggtag tgcactggta tttcagccag ctggacagca atagcagcaa cgacattaac   1140
aagcgggaga tgaagccctt caagcgctac gtgaagaaga agccaagcc caagaaatgt    1200 gcccggcgtt tcaccgacta ctgtgacctg aacaaagaca aggtcatttc actgcctgag   1260
ctgaagggct gcctgggtgt tagcaaagaa gtaggacgcc tcgtctaa               1308
```

<210> SEQ ID NO 3
<211> LENGTH: 670
<212> TYPE: PRT
<213> ORGANISM: Artificial Sequence
<220> FEATURE:
<223> OTHER INFORMATION: protein sequence of SMOC1-Fc fusion protein

<400> SEQUENCE: 3

```
Met Leu Pro Ala Arg Cys Ala Arg Leu Leu Thr Pro His Leu Leu Leu
1               5                   10                  15

Val Leu Val Gln Leu Ser Pro Ala Arg Gly His Arg Thr Thr Gly Pro
            20                  25                  30

Arg Phe Leu Ile Ser Asp Arg Asp Pro Gln Cys Asn Leu His Cys Ser
        35                  40                  45

Arg Thr Gln Pro Lys Pro Ile Cys Ala Ser Asp Gly Arg Ser Tyr Glu
    50                  55                  60

Ser Met Cys Glu Tyr Gln Arg Ala Lys Cys Arg Asp Pro Thr Leu Gly
65                  70                  75                  80

Val Val His Arg Gly Arg Cys Lys Asp Ala Gly Gln Ser Lys Cys Arg
                85                  90                  95

Leu Glu Arg Ala Gln Ala Leu Glu Gln Ala Lys Lys Pro Gln Glu Ala
            100                 105                 110

Val Phe Val Pro Glu Cys Gly Glu Asp Gly Ser Phe Thr Gln Val Gln
        115                 120                 125

Cys His Thr Tyr Thr Gly Tyr Cys Trp Cys Val Thr Pro Asp Gly Lys
    130                 135                 140

Pro Ile Ser Gly Ser Ser Val Gln Asn Lys Thr Pro Val Cys Ser Gly
145                 150                 155                 160

Ser Val Thr Asp Lys Pro Leu Ser Gln Gly Asn Ser Gly Arg Lys Asp
                165                 170                 175

Asp Gly Ser Lys Pro Thr Pro Thr Met Glu Thr Gln Pro Val Phe Asp
            180                 185                 190

Gly Asp Glu Ile Thr Ala Pro Thr Leu Trp Ile Lys His Leu Val Ile
        195                 200                 205

Lys Asp Ser Lys Leu Asn Asn Thr Asn Ile Arg Asn Ser Glu Lys Val
    210                 215                 220

Tyr Ser Cys Asp Gln Glu Arg Gln Ser Ala Leu Glu Glu Ala Gln Gln
225                 230                 235                 240

Asn Pro Arg Glu Gly Ile Val Ile Pro Glu Cys Ala Pro Gly Gly Leu
                245                 250                 255

Tyr Lys Pro Val Gln Cys His Gln Ser Thr Gly Tyr Cys Trp Cys Val
            260                 265                 270

Leu Val Asp Thr Gly Arg Pro Leu Pro Gly Thr Ser Thr Arg Tyr Val
        275                 280                 285
```

```
Met Pro Ser Cys Glu Ser Asp Ala Arg Ala Lys Thr Thr Glu Ala Asp
    290                 295                 300

Asp Pro Phe Lys Asp Arg Glu Leu Pro Gly Cys Pro Glu Gly Lys Lys
305                 310                 315                 320

Met Glu Phe Ile Thr Ser Leu Leu Asp Ala Leu Thr Thr Asp Met Val
                325                 330                 335

Gln Ala Ile Asn Ser Ala Ala Pro Thr Gly Gly Gly Arg Phe Ser Glu
                340                 345                 350

Pro Asp Pro Ser His Thr Leu Glu Glu Arg Val Val His Trp Tyr Phe
            355                 360                 365

Ser Gln Leu Asp Ser Asn Ser Ser Asn Asp Ile Asn Lys Arg Glu Met
    370                 375                 380

Lys Pro Phe Lys Arg Tyr Val Lys Lys Ala Lys Pro Lys Lys Cys
385                 390                 395                 400

Ala Arg Arg Phe Thr Asp Tyr Cys Asp Leu Asn Lys Asp Lys Val Ile
                405                 410                 415

Ser Leu Pro Glu Leu Lys Gly Cys Leu Gly Val Ser Lys Glu Val Gly
                420                 425                 430

Arg Leu Val Ser His His His His His His Ala Ser Asp Lys Thr His
                435                 440                 445

Thr Cys Pro Pro Cys Pro Ala Pro Glu Leu Leu Gly Gly Pro Ser Val
450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
                485                 490                 495

Val Lys Phe Asn Trp Tyr Val Asp Gly Val Glu Val His Asn Ala Lys
                500                 505                 510

Thr Lys Pro Arg Glu Glu Gln Tyr Asn Ser Thr Tyr Arg Val Val Ser
            515                 520                 525

Val Leu Thr Val Leu His Gln Asp Trp Leu Asn Gly Lys Glu Tyr Lys
530                 535                 540

Cys Lys Val Ser Asn Lys Ala Leu Pro Ala Pro Ile Glu Lys Thr Ile
545                 550                 555                 560

Ser Lys Ala Lys Gly Gln Pro Arg Glu Pro Gln Val Tyr Thr Leu Pro
                565                 570                 575

Pro Ser Arg Glu Glu Met Thr Lys Asn Gln Val Ser Leu Thr Cys Leu
            580                 585                 590

Val Lys Gly Phe Tyr Pro Ser Asp Ile Ala Val Glu Trp Glu Ser Asn
        595                 600                 605

Gly Gln Pro Glu Asn Asn Tyr Lys Thr Thr Pro Pro Val Leu Asp Ser
610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
                645                 650                 655

His Asn His Tyr Thr Gln Lys Ser Leu Ser Leu Ser Pro Gly
            660                 665                 670

<210> SEQ ID NO 4
<211> LENGTH: 2149
<212> TYPE: DNA
<213> ORGANISM: Artificial Sequence
<220> FEATURE:
```

<223> OTHER INFORMATION: nucleic acid sequence encoding SMOC1-Fc fusion protein

<400> SEQUENCE: 4

```
atgggctgga gcctgatcct cctgttcctc gtcgctgtgg ctacaggtaa ggggctcaca      60
gtagcaggct tgaggtctgg acatatatat gggtgacaat gacatccact ttgcctttct     120
ctccacaggt ggcgcgcatg ctgcccgcgc gctgcgcccg cctgctcacg ccccacttgc     180
tgctggtgtt ggtgcagctg tccctgctc gcggccaccg caccacaggc cccaggtttc     240
taataagtga ccgtgaccca caatgcaacc tccactgctc caggactcaa cccaaaccca     300
tctgtgcctc tgatggcagg tcctacgagt ccatgtgtga gtaccagcga gccaagtgcc     360
gagacccgac cctgggcgtg gtgcatcgag gtagatgcaa agatgctggc cagagcaagt     420
gtcgcctgga gcgggctcaa gcccggagc aagccaagaa gcctcaggaa gctgtgtttg     480
tcccagagtg tggcgaggat ggctccttta cccaggtgca gtgccatact tacactgggt     540
actgctggtg tgtcaccccg gatgggaagc ccatcagtgg ctcttctgtg cagaataaaa     600
ctcctgtatg ttcaggttca gtcaccgaca agcccttgag ccagggtaac tcaggaagga     660
aagatgacgg gtctaagccg acacccacga tggagaccca gccggtgttc gatggagatg     720
aaatcacagc cccaactcta tggattaaac acttggtgat caaggactcc aaactgaaca     780
acaccaacat aagaaattca gagaaagtct attcgtgtga ccaggagagg cagagtgctc     840
tggaagaggc ccagcagaat ccccgtgagg gtattgtcat ccctgaatgt gcccctgggg     900
gactctataa gccagtgcaa tgccaccagt ccactggcta ctgctggtgt gtgctggtgg     960
acacagggcg cccgctgcct gggacctcca cacgctacgt gatgcccagt tgtgagagcg    1020
acgccagggc caagactaca gaggcggatg accccttcaa ggacagggag ctaccaggct    1080
gtccagaagg gaagaaaatg gagtttatcc cagcctact ggatgctctc accactgaca    1140
tggttcaggc cattaactca gcagcgccca ctggaggtgg gaggttctca gagccagacc    1200
ccagccacac cctggaggag cgggtagtgc actggtatt cagccagctg acagcaata    1260
gcagcaacga cattaacaag cgggagatga agcccttcaa cgctacgtg aagaagaaag    1320
ccaagcccaa gaaatgtgcc cggcgtttca ccgactactg tgacctgaac aaagacaagg    1380
tcatttcact gcctgagctg aagggctgcc tgggtgttag caaagaagta ggacgcctcg    1440
tctcacatca tcaccatcac cacgctagcg acaaaactca cacatgccca ccgtgcccag    1500
cacctgaact cctgggggga ccgtcagtct tcctcttccc cccaaaaccc aaggacaccc    1560
tcatgatctc ccggaccct gaggtcacat gcgtggtggt ggacgtgagc cacgaagacc    1620
ctgaggtcaa gttcaactgg tacgtggacg gcgtggaggt gcataatgcc aagacaaagc    1680
cgcgggagga gcagtacaac agcacgtacc gtgtggtcag cgtcctcacc gtcctgcacc    1740
aggactggct gaatggcaag gagtacaagt gcaaggtctc caacaaagcc ctcccagccc    1800
ccatcgagaa aaccatctcc aaagccaaag gcagccccg agaaccacag gtgtacaccc    1860
tgcccccatc ccgggaggag atgaccaaga accaggtcag cctgacctgc ctggtcaaag    1920
gcttctatcc cagcgacatc gccgtggagt gggagagcaa tggcagccg agaacaact    1980
acaagaccac gcctcccgtg ctggactccg acggctcctt cttcctctat agcaagctca    2040
ccgtggacaa gagcaggtgg cagcagggga acgtcttctc atgctccgtg atgcatgagg    2100
ctctgcacaa ccactacacg cagaagagcc tctccctgtc cccgggtaa               2149
```

METHODS AND COMPOSITIONS FOR IMPROVING GLUCOSE METABOLISM

CROSS REFERENCE TO RELATED APPLICATIONS

The present application is a § 371 National Phase Application of PCT/AU2016/051020, filed Oct. 28, 2016, which application claims priority from Australian provisional application AU 2015904460, filed Oct. 30, 2015, the entire contents of which are hereby incorporated in their entirety.

The present application claims priority from Australian provisional application AU 2015904460, the entire contents of which are hereby incorporated in their entirety.

FIELD OF THE INVENTION

The present invention relates to compositions, methods and kits for promoting glucose clearance in an individual. In particular, the compositions, methods and kits are particularly useful, but not limited to, the treatment of insulin resistance or type 2 diabetes.

BACKGROUND OF THE INVENTION

Insulin resistance (IR) is a condition in which the body's cells become less sensitive to the glucose-lowering effects of the hormone insulin. The common underlying causes of insulin resistance are largely unidentified, however both inherited and acquired influences are likely to be involved. Environmental factors such as physical inactivity, abdominal obesity, diet (e.g., high calorie intake), medications (e.g., Cortisol), hyperglycaemia (glucose toxicity), increased free fatty acids, and the aging process may also contribute. The most common type of insulin resistance is associated with obesity resulting in a condition known as metabolic syndrome.

In an insulin-resistant person, normal levels of insulin do not have the same effect in controlling blood glucose levels. During the compensated phase in insulin resistance insulin levels are higher, and blood glucose levels are largely maintained. Therefore, in most people with insulin resistance there are normal levels of glucose in the blood but high levels of insulin in the blood. If compensatory insulin secretion fails, then either fasting (impaired fasting glucose) or postprandial (impaired glucose tolerance) blood glucose concentrations increase. Eventually, Type 2 diabetes occurs when blood glucose levels become higher throughout the day as the resistance increases and compensatory insulin secretion fails.

In pre-diabetes, insulin becomes less effective at stimulating metabolism of glucose. Pre-diabetics may be detectable as early as 20 years before diabetic symptoms become evident. Studies have shown that although patients typically show very few symptoms, long-term physiological damage is already occurring at this stage. Up to 60% of these individuals will progress to Type 2 diabetes within 10 years.

Diabetes mellitus is a metabolic disease that is brought about by either the insufficient production of insulin or the inability of the body to properly respond to insulin. Insulin is produced by the pancreas and is the principal hormone that regulates the uptake of glucose from the blood into cells and inhibits the production of glucose from the liver. Therefore deficiency of insulin production or the insensitivity to its actions plays a key role in all forms of diabetes. Insulin deficiencies, the insensitivity of insulin receptors, or a combination of both play a central role in both Type 1 and Type 2 forms of diabetes mellitus. Type 1 diabetes mellitus is caused by a decrease in the number of insulin-producing cells in the islets of Langerhans in the pancreas. Type 2 diabetes mellitus is generally characterized by the body's resistance to insulin, caused by the loss or diminished function of insulin receptors that mediate the entrance of insulin into the body's cells. Type 2 diabetes occurs commonly in association with other disorders such as hypertension, dyslipidaemia (includes high LD1 cholesterol, low HDL cholesterol, and high triglycerides) and hypercoagulability. All these problems usually occur in association with obesity, especially abdominal obesity.

There exists a need for new and/or improved treatments for conditions associated with impaired response to insulin and/or glucose metabolism.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The invention provides a method of promoting blood glucose clearance in an individual, the method comprising administering SMOC1, a biologically active variant or analog thereof to the individual, thereby promoting blood glucose clearance in the individual.

The invention provides a method of accelerating the reduction or depletion of blood glucose in an individual, the method comprising administering SMOC1, a biologically active variant or analog thereof to the individual, thereby accelerating the reduction or depletion of blood glucose in the individual.

Preferably, the individual has an impaired ability to clear glucose from the blood. Typically, the individual displays a level of insulin resistance.

The invention provides a method of promoting blood glucose clearance in an individual, the method comprising
  identifying an individual with (a) an impaired ability to clear glucose from the blood, or (b) an elevated fasting level of SMOC1, glucose or insulin,
  administering SMOC1, a biologically active variant or analog thereof to the individual,
  thereby promoting blood glucose clearance in the individual.

The invention also provides a method of increasing glycaemic control in an individual, the method comprising administering SMOC1, a biologically active variant or analog thereof to the individual, thereby increasing glycaemic control in the individual.

The invention also provides a method for treating or preventing a disorder associated with, or arising from, increased blood glucose levels in an individual, the method comprising administering SMOC1, a biologically active variant or analog thereof to the individual, thereby treating or preventing a disorder associated with, or arising from, increased blood glucose in the individual.

The present invention provides a method of promoting blood glucose clearance in an individual, the method comprising the step of administering a composition to the subject, wherein the composition comprises, consists essentially of or consists of SMOC1, a biologically active variant or analog thereof, and a pharmaceutically acceptable diluent, excipient or carrier.

In any method or use of the invention described herein, SMOC1, a biologically active variant or analog thereof may be administered systemically. Alternatively, SMOC1, a biologically active variant or analog thereof may be formulated for oral administration and then administered orally in a method or use of the invention described herein.

The invention provides a pharmaceutical composition for promoting blood glucose clearance in an individual comprising SMOC1, a biologically active variant or analog thereof, and a pharmaceutically acceptable diluent, excipient or carrier. In one embodiment, the only active ingredient present in the composition is SMOC1, a biologically active variant or analog thereof.

The invention provides a pharmaceutical composition for promoting blood glucose clearance in an individual comprising as an active ingredient SMOC1, a biologically active variant or analog thereof and a pharmaceutically acceptable diluent, excipient or carrier. In one embodiment, the only active ingredient present in the composition is SMOC1, a biologically active variant or analog thereof.

The invention provides a pharmaceutical composition for promoting blood glucose clearance in an individual comprising as a main ingredient SMOC1, a biologically active variant or analog thereof, and a pharmaceutically acceptable diluent, excipient or carrier. In one embodiment, the only active ingredient present in the composition is SMOC1, a biologically active variant or analog thereof.

The invention also provides SMOC1, a biologically active variant or analog thereof for use in the treatment of an individual that has an impaired ability to clear glucose from the blood The invention also provides a pharmaceutical composition comprising SMOC1, a biologically active variant or analog thereof, and a pharmaceutically acceptable diluent, excipient or carrier for use in promoting blood glucose clearance, or accelerating a reduction or depletion of blood glucose, in an individual.

The present invention also provides use of SMOC1, a biologically active variant or analog thereof, in the manufacture of a medicament for promoting blood glucose clearance in an individual in need thereof.

The present invention also provides a composition comprising SMOC1, a biologically active variant or analog thereof for use in the treatment of individuals with (a) an impaired ability to clear glucose from the blood, (b) an elevated fasting level of SMOC1, glucose or insulin, or (c) any other condition or disease described herein.

The present invention also provides a composition comprising SMOC1, a biologically active variant or analog thereof, and a pharmaceutically acceptable carrier, diluent or excipient.

The present invention also provides a composition comprising as a main ingredient or active ingredient SMOC1, a biologically active variant or analog thereof. Preferably, the only active ingredient in the composition is SMOC1, a biologically active variant or analog thereof.

The present invention also provides a fusion protein comprising an amino acid sequence of SMOC1, a biologically active variant or analog thereof. Preferably, the fusion protein comprises a first amino acid sequence of SMOC1 and a second amino acid sequence of SMOC1, a biologically active variant or analog thereof.

The present invention also provides a fusion protein comprising an Fc portion of an antibody and a SMOC1 protein. The SMOC1 protein may be SMOC1, a biologically active variant or analog thereof. The Fc portion may be derived from, for example, a human IgG antibody, such as an IgG1 or IgG2 antibody.

The present invention also provides a fusion protein comprising or consisting of the sequence set forth in SEQ ID NO: 3 (SMOC1-Fc, IgG1), or a biologically active variant or analog thereof. The biologically active variant or analog of the fusion protein may have, for example, at least 70%, at least 80%, at least 85%, at least 90%, at least 91%, at least 92%, at least 93%, at least 94%, at least 95%, at least 96%, at least 97%, at least 98% or at least 99% sequence identity to the sequence set forth in SEQ ID NO: 3. The biologically active variant or analog also retains the ability to promote glucose clearance.

The present invention also provides a nucleic acid comprising, consisting essentially of or consisting of a nucleotide sequence shown in SEQ ID NO: 4.

The present invention also provides a vector, preferably an expression vector, comprising a nucleotide sequence as shown in SEQ ID NO: 4.

The present invention also provides a host cell comprising a nucleic acid comprising, consisting essentially of or consisting of a nucleotide sequence shown in SEQ ID NO: 4, or a vector, preferably an expression vector, comprising a nucleotide sequence as shown in SEQ ID NO: 4.

The present invention also provides a method for diagnosing an individual as having type 2 diabetes, or at risk of developing same, the method comprising:
- providing a test sample of peripheral blood from an individual for whom a diagnosis of type 2 diabetes is to be determined;
- assessing the test sample for the level of SMOC1, thereby forming a test sample profile;
- providing a control profile containing data on the level of SMOC1 in peripheral blood of an individual without type 2 diabetes;
- comparing the test sample profile with the control profile to identify whether there is a difference in the level of SMOC1 as between the test sample profile and the control profile;
- determining that the individual has type 2 diabetes, or is at risk of developing the same, where the level of SMOC1 in the test sample profile is higher than the control profile;
- determining that the individual does not have type 2 diabetes, or is not at risk of developing the same, where the level of SMOC1 in the test sample profile is the same or lower than the control profile.

The present invention also provides a method for diagnosing an individual as having type 2 diabetes, or at risk of developing same, the method comprising:
- providing a test sample of peripheral blood from an individual for whom a diagnosis of type 2 diabetes is to be determined;
- assessing the test sample for the level of SMOC1, thereby forming a test sample profile;
- providing a control profile containing data on the level of SMOC1 in peripheral blood of an individual with type 2 diabetes;
- comparing the test sample profile with the control profile to identify whether there is a difference in the level of SMOC1 as between the test sample profile and the control profile;
- determining that the individual does not have type 2 diabetes, or is not at risk of developing the same, where the level of SMOC1 in the test sample profile is lower than the control profile;

determining that the individual has type 2 diabetes, or is at risk of developing the same, where the level of SMOC1 in the test sample profile is the same or higher than the control profile.

As used herein, unless otherwise specified, reference to SMOC1 includes reference to a fusion protein comprising SMOC1, for example, a fusion protein comprising an Fc portion of an antibody and a SMOC1 protein.

In any aspect of the present invention, the individual may be one that has been identified as having an impaired ability to clear glucose from the blood, displays a level of insulin resistance and/or diagnosed with type 2 diabetes.

In any aspect of the present invention, the individual may be one that has been identified as having an elevated level of circulating insulin and/or SMOC1. Preferably, the level of circulating insulin and/or SMOC1 that is elevated is at a fasting state or is a basal level.

In any aspect of the present invention, SMOC1 may be administered prior to an event that raises the fasting or basal blood glucose level in the individual. Typically, SMOC1 is administered before feeding or pre-prandial. Typically, SMOC1 is administered during a fasting period. Preferably, SMOC1 is administered to an individual that hasn't consumed any calories for 4, 3, 2 or 1 hour.

In any aspect of the present invention, SMOC1 may be human SMOC1. Preferably, human SMOC1 has an amino acid sequence shown in SEQ ID NO: 1.

In any aspect of the present invention, SMOC1 may be isolated, recombinant, synthetic, purified or substantially purified.

In any statement of the invention above, reference to SMOC1 may also include reference to a biologically active variant or analog of SMOC1. A biologically active variant or analog of SMOC1, preferably human SMOC1, is a polypeptide that may have, for example, at least 70%, at least 80%, at least 85%, at least 90%, at least 91%, at least 92%, at least 93%, at least 94%, at least 95%, at least 96%, at least 97%, at least 98% or at least 99% sequence identity to SEQ ID NO: 1, and also retains the biological activity or ability to promote glucose clearance. The ability to promote glucose clearance may be measured by any method as described herein or known in the art.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

(A) Male C57Bl/6J mice aged 12 weeks were fed a Chow diet or a high-fat diet (HFD) for 6 weeks. Hepatocytes were isolated and protein secretion from the liver was assessed by iTRAQ protein labelling and tandem mass spectrometry. (B) Male C57Bl/6J mice were injected with glucose (2 g/kg body mass) and blood samples were obtained from a tail cut, the plasma collected after centrifugation and SMOC1 protein determined by immunoblot and normalized to protein loading (stain-free gel. N=3 mice).

Figure 2:
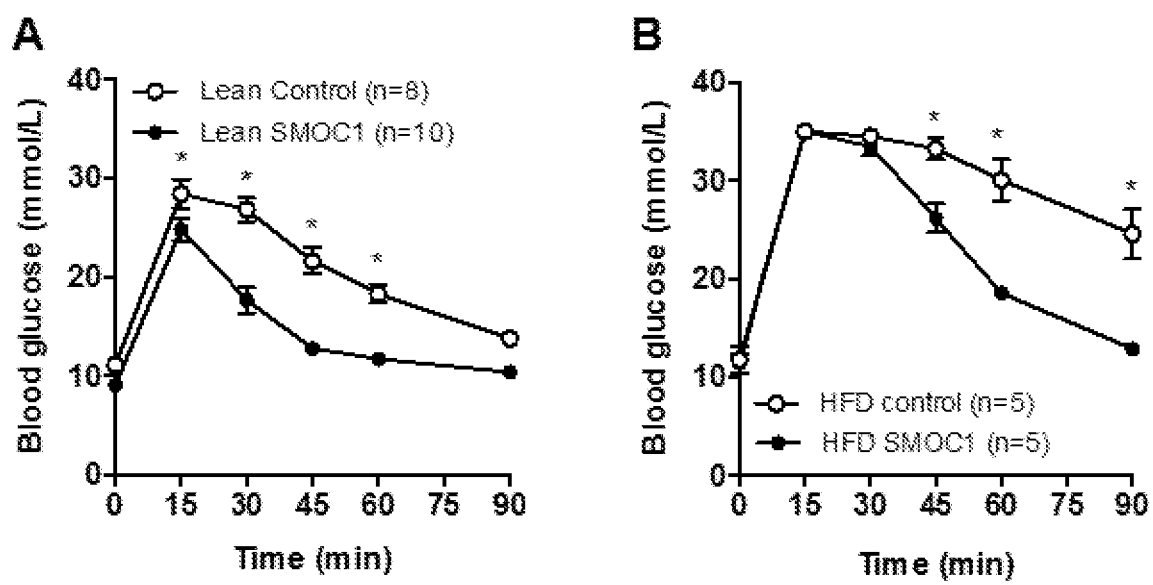

FIG. 2. Effect of SMOC1 on plasma glucose responses to intraperitoneal glucose administration.

Male C57Bl/6J mice aged 12 weeks and fed a (A) Chow diet (Lean) or (B) a high-fat diet (HFD). SMOC1 or control solution were injected 2 h prior to glucose administration. Blood samples were obtained before (0 min) and at 15 min intervals after glucose administration (2 g/kg body mass). Results from two independent experiments (Lean: n=9 Control, n=10 SMOC1, HFD: n=5 Control, n=5 SMOC1). Statistical analysis was performed by two-way repeated measures analysis of variance with Bonferroni post hoc testing. *P<0.05 vs corresponding time point between Control and SMOC1.

Figure 3:
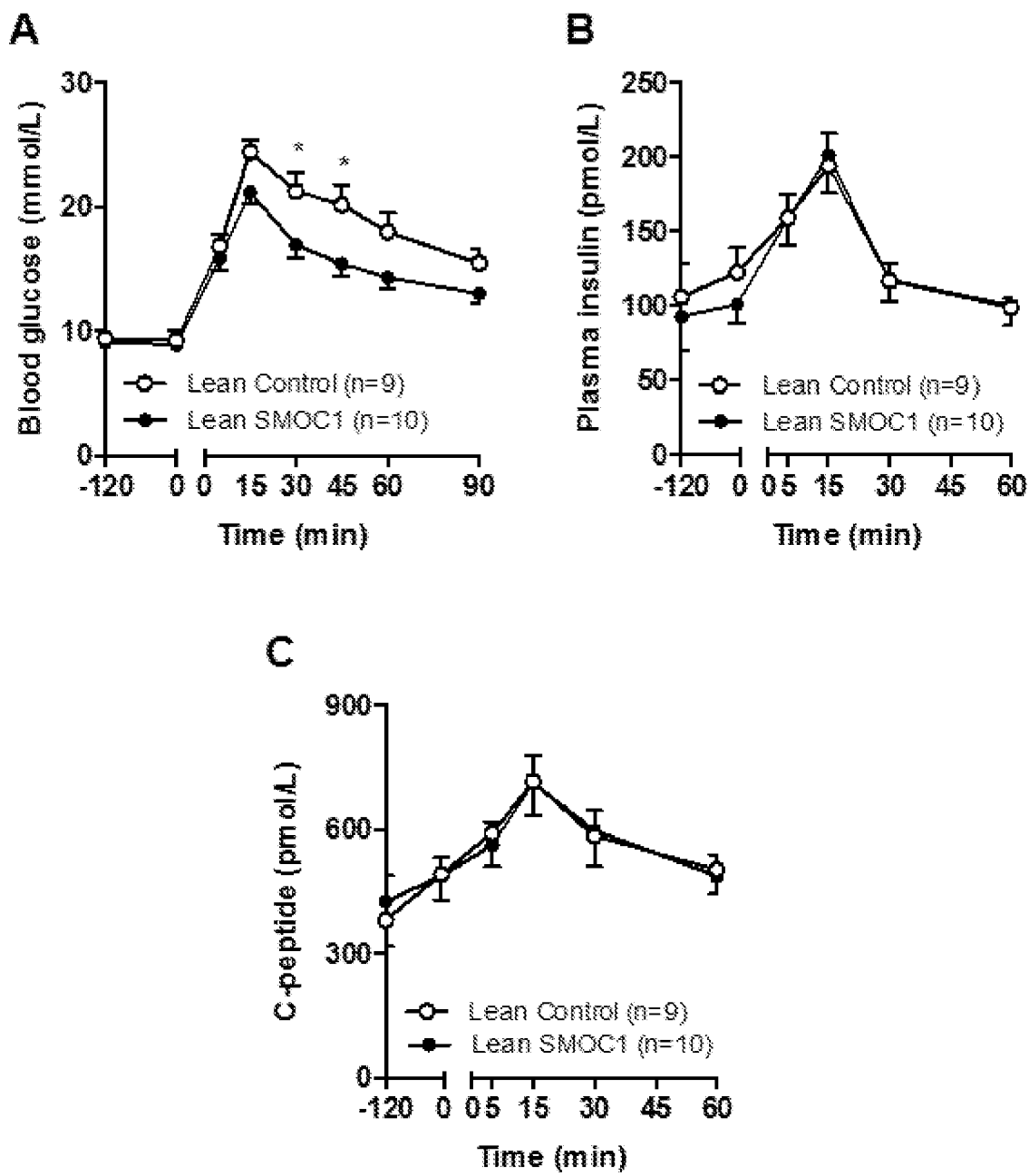

FIG. 3. Effect of SMOC1 on plasma glucose and insulin responses to oral glucose administration in lean mice.

Male C57Bl/6J mice aged 12 weeks and fed a Chow diet (Lean). SMOC1 or control solution were injected 2 h prior to glucose administration. Blood samples were obtained before SMOC1 administration (−120 min), before glucose administration (0 min), and at 15 min intervals after glucose administration (50 pg glucose). (A) Blood glucose, (B) plasma insulin and (C) plasma C-peptide levels. Results from two independent experiments (n=9 Control, n=10 SMOC1). Statistical analysis was performed by two-way repeated measures analysis of variance with Bonferroni post hoc testing. *P<0.05 vs corresponding time point between Control and SMOC1.

Figure 4:
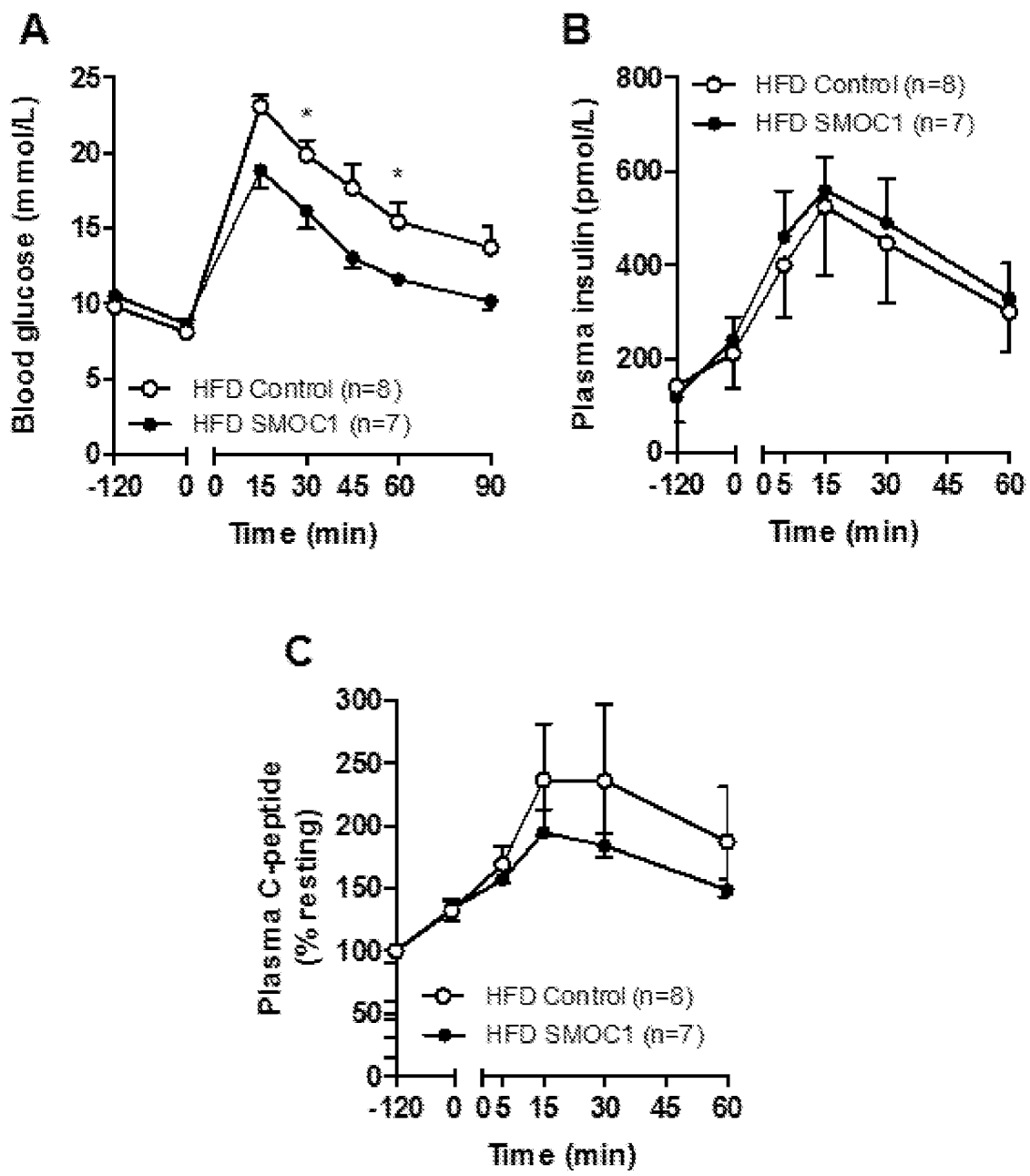

FIG. 4. Effect of SMOC1 on plasma glucose and insulin responses to oral glucose administration in obese mice.

Male C57Bl/6J mice aged 12 weeks and fed a high-fat diet (HFD). SMOC1 or control solution were injected 2 h prior to glucose administration. Blood samples were obtained before SMOC1 administration (−120 min), before glucose administration (0 min), and at 15 min intervals after glucose administration (50 μg glucose). (A) Blood glucose, (B) plasma insulin and (C) plasma C-peptide levels. Results from two independent experiments (n=8 Control, n=7 SMOC1). Statistical analysis was performed by two-way repeated measures analysis of variance with Bonferroni post hoc testing. *P<0.05 vs corresponding time point between Control and SMOC1.

Figure 5:
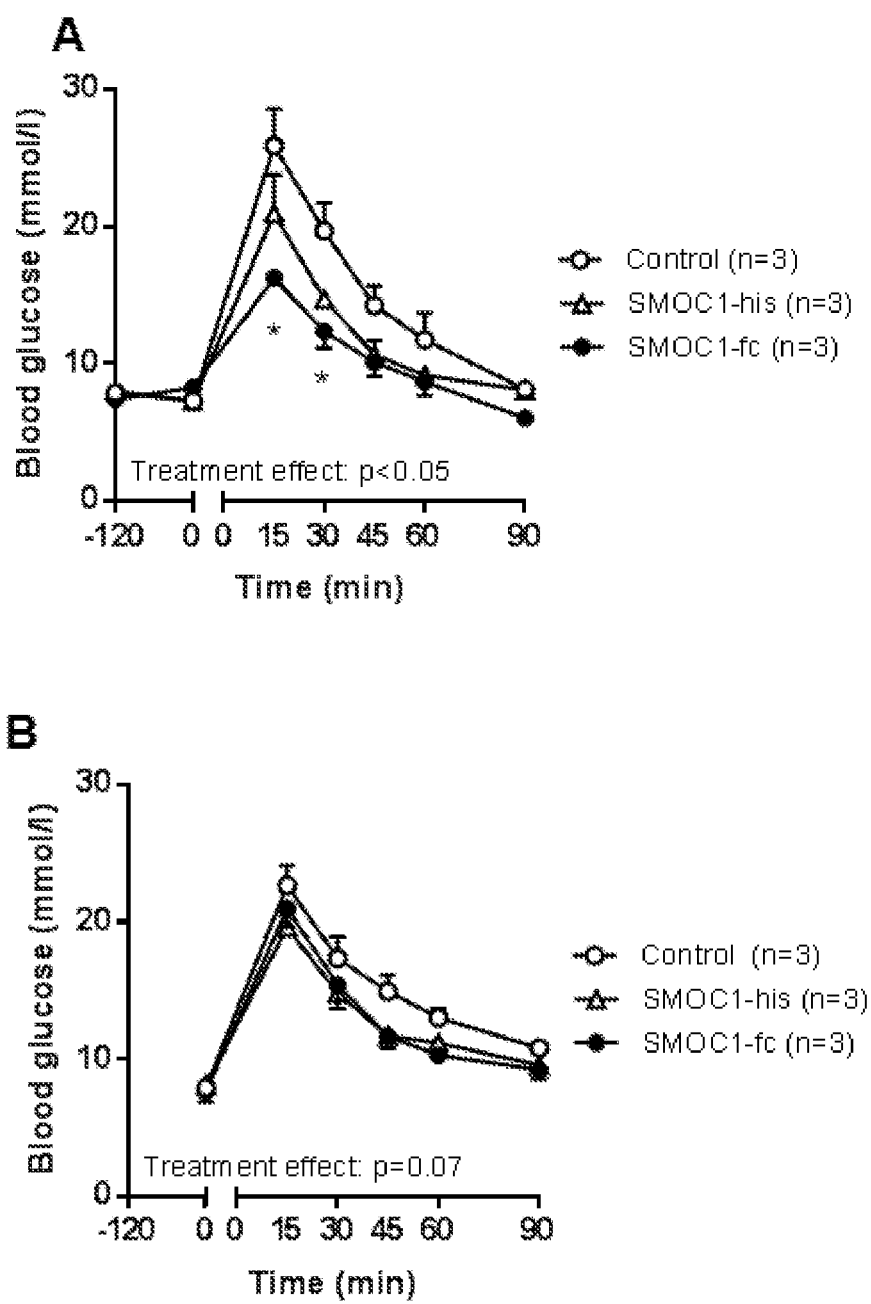

FIG. 5. Effect of SMOC1 and SMOC1-fc on plasma glucose responses to glucose administration.

Male C57Bl/6J mice aged 15 weeks. SMOC1-his, SMOC1-fc or control solution were injected. Blood samples were obtained before SMOC1/control administration (−120 min), before glucose administration (0 min), and at 15 min intervals after glucose administration (2 g/kg body mass). (A) Blood glucose immediately after SMOC1/control injection, (B) blood glucose levels 24 h after SMOC1/control injection. Results from one experiments (n=3 per group). Statistical analysis was performed by two-way repeated measures analysis of variance with Bonferroni post hoc testing. *P<0.05 vs corresponding time point between Control and SMOC1-fc.

Figure 6:
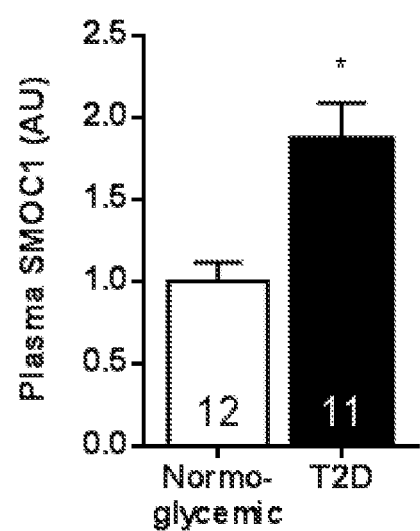

FIG. 6. SMOC1 is upregulated in individuals with type 2 diabetes compared with normoglycemic subjects.

Plasma SMOC1 levels in obese humans without (normoglycemic, n=12) or with type 2 diabetes (T2D, n=11). *P=0.005 vs. normoglycemic.

Figure 7:
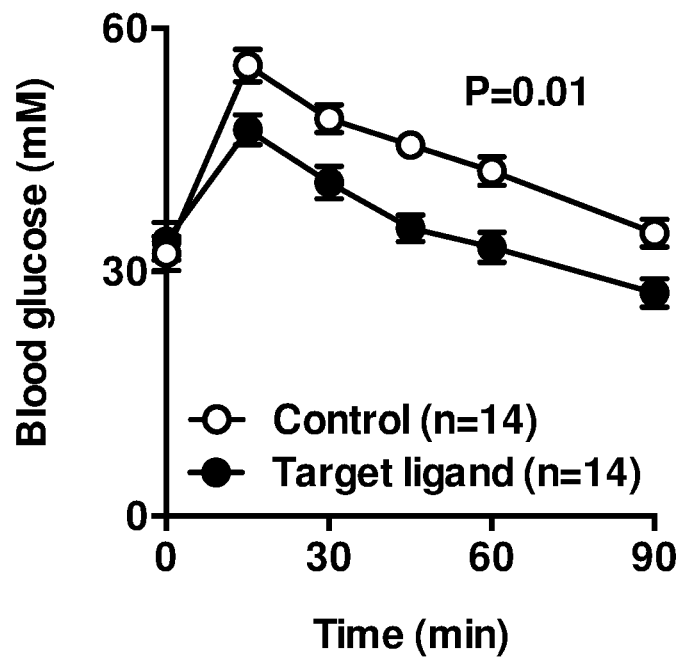
Figure 7:
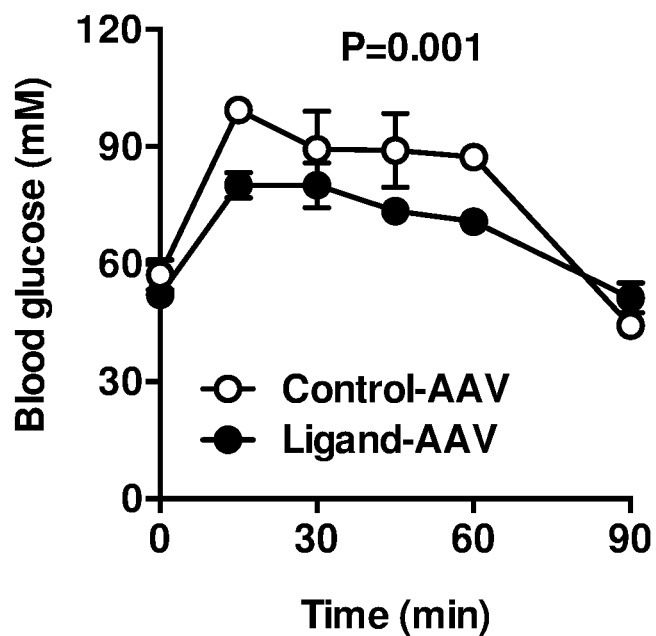

FIG. 7. SMOC1 improves glucose tolerance in diabetic db/db mice.

(A) Female db/db mice aged 10 weeks. Mice were injected intraperitoneally with SMOC1 (3 mg/kg) protein ('target ligand') or control protein solution. Blood samples were obtained before SMOC1/control administration (−120 min), before glucose administration (0 min) and at 15 min intervals after glucose administration (50 mg/mouse). Randomized cross over design with 5 days between trials. N=14 for control, n=14 for SMOC1.

(B) Female db/db mice aged 10 weeks. Mice were injected intravenously with an adenoassociated virus (AAV) encoding GFP or with an AAV encoding a SMOC1/GFP fusion. Glucose tolerance was assessed as described for part A) at 18 weeks. N=3 for Control-AAV, n=3 for SMOC1-AAV ('ligand-AAV').

SUMMARY OF SEQUENCES DESCRIBED HEREIN

SEQ ID NO: 1—An example of a human SMOC1 amino acid sequence
SEQ ID NO: 2—An example of a human SMOC1 nucleotide sequence
SEQ ID NO: 3—SMOC1-Fc-3'His amino acid sequence
SEQ ID NO: 4—SMOC1-Fc-3'His nucleotide sequence

DETAILED DESCRIPTION OF THE EMBODIMENTS

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

An inability to efficiently clear glucose from the blood is a major defect of individuals with insulin resistance (pre-diabetes) and type 2 diabetes. The results described herein demonstrate that SMOC1 can improve glucose clearance in lean, insulin sensitive mice and mice rendered overweight and insulin resistant (pre-diabetic) by high-fat feeding.

Without being bound by any theory or mode of action, SMOC1 may not induce these beneficial effects by enhancing insulin secretion, but rather, the experimental data indicate that SMOC1 acts as either (1) an insulin sensitizer or (2) a modulator of glucose clearance that works only when blood glucose levels are elevated (such as after a meal). If this is the case, then methods and compounds of the present invention are also useful for increasing insulin-stimulated blood glucose clearance. Methods and compounds of the invention can be used to increase sensitivity to insulin. Increased glucose uptake provides means for reducing blood glucose levels in individuals with elevated glucose levels, such as in hyperglycaemia or diabetes, or in individuals with deficiencies in achieving or maintaining glucose homeostasis. Therefore, methods and compounds of the present invention are useful for treating hyperglycaemia and diabetes by increasing insulin sensitivity, and reducing blood glucose levels.

The invention described herein is clinically relevant and advantageous as SMOC1 enhances blood glucose clearance without causing hypoglycaemia (low blood glucose) in a fasting state, which is a problem with many existing diabetes medications. In other words, SMOC1 does not cause significant reduction in the basal glucose level of an individual.

A further advantage of the present invention is that the beneficial effects observed on glucose clearance or depletion does not require exogenous insulin or C-peptide administration.

Disruption in the normal regulation of glucose can lead to blood glucose levels deviating from, i.e., elevated or low compared to, normal blood glucose levels. Chronically elevated blood glucose levels, characteristic, for example, of hyperglycaemia, diabetes, can impose multiple detrimental effects on various organs, tissue, and systems of the body. Diabetes, hyperglycaemia, or elevated blood glucose levels are associated with numerous disorders and conditions, including accelerated atherosclerosis, increased chronic heart disease, myocardial infarction, stroke, microangiopathy, damage to blood vasculature, peripheral vascular disease leading to decreased circulation in the arms and legs, macrovascular complication, ocular disorders, such as, for example, diabetic retinopathy, macular degeneration, cataracts, etc., kidney disorders, including, diabetic nephropathy, kidney damage, etc., damage to nerves and other neuropathies, including diabetic neuropathy, peripheral neuropathy, damage to nerves of the autonomic nervous system, etc., hyperinsulinaemia, hyperlipidaemia, insulin resistance, skin and connective tissue disorders, foot wounds and ulcerations, diabetic ketoacidosis, etc.

Altered or impaired glucose regulation, and the presence of or risk for development of disorders including diabetes, hyperglycaemia, etc., can be identified by measurement of circulating glucose or determination of blood/plasma glucose levels. Blood glucose levels are most often measured by a fasting blood glucose test, a random blood glucose test, or an oral glucose tolerance test.

The methods and compositions of the invention described herein are for promoting, accelerating, increasing the rate of, or improving the clearance, depletion or reduction in blood glucose. Typically, that means that at each time point after an event that leads to an increase in the fasting or basal glucose level of an individual, the level of blood glucose in an individual who has received SMOC1 is less than in an individual that has not received SMOC1 (i.e. a control individual).

A significant benefit of the invention as described herein is at 30, 45, 60 and 90 minutes after an elevation in fasting or basal blood glucose levels. Typically, the % decrease of maximal blood glucose levels 30, 60, 45 or 90 minutes post-event that raises the fasting or basal blood glucose (i.e. post-prandial) is at least about 3%, at least about 5%, at least about 10%, at least about 20%, at least about 25%, at least about 30%, at least about 35%, at least about 40%, at least about 45% of control (i.e. without SMOC1 administered). The % decrease may be any value shown in the Examples.

In any aspect of the present invention, SMOC1 may be administered prior to an event that raises the fasting or basal blood glucose level in the individual. Typically, SMOC1 is administered to an individual before feeding or pre-prandial. Typically, SMOC1 is administered to the individual in a fasting period. Preferably, SMOC1 is administered to an individual that hasn't consumed any calories for 4 hours, 3 hours, 2 hours or 1 hour.

The term "glycaemic control" refers to maintaining, restoring, or achieving normal or near normal blood glucose levels.

The term "hyperglycaemia" as used herein refers generally to blood glucose concentrations or levels that are above normal. Hyperglycaemia can be determined by any measure accepted and utilized by those of skill in the art. Currently, in humans, normal blood glucose is considered to be between about 70 and 120 mg/dl (3.9-6.6 mmol/L), but varies depending on the fasting state. Before a meal, blood glucose can range from about 80 to 120 mg/dl (4.4-6.6 mmol/L), whereas two hours after a meal, blood glucose can be at or below about 180 mg/dl (10 mmol/L). Additionally, in fasted individuals, normal blood glucose is below about 110 mg/dl (6.1 mmol/L). A subject having a blood glucose value of about 126 mg/dl (7 mmol/L) or greater is generally considered hyperglycaemic, and a subject whose blood glucose is above about 200 mg/dl (11.1 mmol/L) is generally considered diabetic.

As used herein, the term "condition" refers to a disruption of or interference with normal function, and is not to be limited to any specific condition, and will include diseases or disorders.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians. For example, prevention of an impaired ability to clear blood glucose could be determined by a medical practitioner using known methods.

The terms "treatment" or "treating" of a subject includes the application or administration of SMOC1, fusion protein or pharmaceutical composition of the invention to a subject (or application or administration of a SMOC1, fusion protein or pharmaceutical composition of the invention to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being.

The existence of, improvement in, treatment of or prevention of a disease associated with, or arising from, an impaired ability to clear glucose from the blood may be determined by any clinically or biochemically relevant method of the subject or a biopsy therefrom. For example, a parameter measured may be the presence of a certain level of glucose in the blood or rate or degree of decline of glucose in the blood after a glucose challenge. Typically, that includes blood glucose levels measured by a fasting blood glucose test, a random blood glucose test, or an oral glucose tolerance test.

As used herein, the term "subject" or "individual" shall be taken to mean any animal including humans, for example a mammal. Exemplary subjects include but are not limited to humans and non-human primates. For example, the subject is a human.

Although the invention finds application in humans, the invention is also useful for therapeutic veterinary purposes. The invention is useful for domestic or farm animals such as cattle, sheep, horses and poultry; for companion animals such as cats and dogs; and for zoo animals.

A subject or individual "in need thereof" includes a subject or individual that has (a) an impaired ability to clear glucose from the blood, (b) an elevated fasting level of SMOC1, glucose or insulin, (c) any other condition or disease described herein including, but not limited to, insulin resistance, diabetes (preferably type 2 diabetes).

While the invention is particularly useful for individuals "in need thereof" as outlined above, in one aspect the invention is also contemplated for use in the modulation of blood glucose levels in normal individuals (e.g. individuals without any detectable insulin resistance).

SMOC1

As used herein unless stated otherwise SMOC1, also known as SPARC related modular calcium binding 1 or Secreted Modular Calcium-binding protein 1, includes to all isoforms, orthologs, paralogs or homologs of human SMOC1. Preferably, the SMOC1 as used herein is human SMOC1. Human SMOC1 may comprise, consist essentially of or consist of an amino acid sequence shown in SEQ ID NO: 1 or encoded by the nucleotide sequence shown in SEQ ID NO: 2. The amino acid and nucleotide sequence of human SMOC1 is also accessible in the NCBI database using the accession number Nm_001034852.1.

SMOC1 is a secreted modular protein containing an EF-hand calcium-binding domain and further includes two thyroglobulin-like domains and a follistatin-like domain. SMOC-1 is a glycoprotein with a calcium-dependent conformation. SMOC1 binds to several proteins, including C-reactive protein (CRP), fibulin-1 and vitronectin. TGF-β signaling through ALK5 and SMAD 2/3 activation leads to inhibition of angiogenesis, while TGF-β signaling through ALD1 and SMAD1/5/8 activation results in potentiation of angiogenesis. SMOC1 acts as a negative regulator of ALK5/SMAD2 and tips TGF-β towards ALK1 activation, thereby promoting endothelial cell proliferation and angiogenesis.

The term "isolated" in relation to a protein or polypeptide means that by virtue of its origin or source of derivation is not associated with naturally-associated components that accompany it in its native state; is substantially free of other proteins from the same source. A protein may be rendered substantially free of naturally associated components or substantially purified by isolation, using protein purification techniques known in the art. By "substantially purified" is meant the protein is substantially free of contaminating agents, e.g., at least about 70% or 75% or 80% or 85% or 90% or 95% or 96% or 97% or 98% or 99% free of contaminating agents.

The term "recombinant" shall be understood to mean the product of artificial genetic recombination. Accordingly, in the context of a recombinant protein comprising or consisting of SMOC1, this term does not encompass a SMOC1 naturally-occurring within a subject's body. However, if such a protein is isolated, it is to be considered an isolated protein comprising or consisting of SMOC1. Similarly, if nucleic acid encoding the protein is isolated and expressed using recombinant means, the resulting protein is a recombinant protein comprising or consisting of SMOC1 A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulphide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

Also contemplated for use in the invention is a biologically active variant or analog of SMOC1, preferably human, that is a polypeptide or peptidomimetic that may have, for example, at least 70%, at least 80%, at least 85%, at least 90%, at least 91%, at least 92%, at least 93%, at least 94%, at least 95%, at least 96%, at least 97%, at least 98% or at least 99% sequence identity to SEQ ID NO: 1, which also retains the biological activity or ability to promote glucose clearance. The ability to promote glucose clearance may be measured by any method as described herein or known in the art. The biologically active variant or analog may contain one or more conservative amino acid substitutions, or non-native amino acid substitutions.

"Percent (%) amino acid sequence identity" or "percent (%) identical" with respect to a polypeptide sequence, i.e. a polypeptide, protein or fusion protein of the invention defined herein, is defined as the percentage of amino acid residues in a candidate sequence that are identical with the amino acid residues in the specific polypeptide of the invention, after aligning the sequences and introducing gaps, if necessary, to achieve the maximum percent sequence identity, and not considering any conservative substitutions as part of the sequence identity.

Those skilled in the art can determine appropriate parameters for measuring alignment, including any algorithms (non-limiting examples described below) needed to achieve maximal alignment over the full-length of the sequences being compared. When amino acid sequences are aligned, the percent amino acid sequence identity of a given amino acid sequence A to, with, or against a given amino acid sequence B (which can alternatively be phrased as a given amino acid sequence A that has or comprises a certain percent amino acid sequence identity to, with, or against a given amino acid sequence B) can be calculated as: percent amino acid sequence identity=X/Y100, where X is the number of amino acid residues scored as identical matches by the sequence alignment program's or algorithm's alignment of A and B and Y is the total number of amino acid residues in B. If the length of amino acid sequence A is not equal to the length of amino acid sequence B, the percent amino acid sequence identity of A to B will not equal the percent amino acid sequence identity of B to A.

In calculating percent identity, typically exact matches are counted. The determination of percent identity between two sequences can be accomplished using a mathematical algorithm. A nonlimiting example of a mathematical algorithm utilized for the comparison of two sequences is the algorithm of Karlin and Altschul (1990) Proc. Natl. Acad. Sci. USA 87:2264, modified as in Karlin and Altschul (1993) Proc. Natl. Acad. Sci. USA 90:5873-5877. Such an algorithm is incorporated into the BLASTN and BLASTX programs of Altschul et al. (1990) J. Mol. Biol. 215:403. To obtain gapped alignments for comparison purposes, Gapped BLAST (in BLAST 2.0) can be utilized as described in Altschul et al. (1997) Nucleic Acids Res. 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection. Another non-limiting example of a mathematical algorithm utilized for the comparison of sequences is the ClustalW algorithm (Higgins et al. (1994) Nucleic Acids Res. 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting examples of a software program useful for analysis of ClustalW alignments is GENEDOC™ or JalView. GENEDOC™ allows assessment of amino acid (or DNA) similarity and identity between multiple proteins. Another non-limiting example of a mathematical algorithm utilized for the comparison of sequences is the algorithm of Myers and Miller (1988) CABIOS 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM 120 weight residue table, a gap length penalty of 12, and a gap penalty of 4 can be used.

The polypeptide desirably comprises an amino end and a carboxyl end. The polypeptide can comprise D-amino acids, L-amino acids or a mixture of D- and L-amino acids. The D-form of the amino acids, however, is particularly preferred since a polypeptide comprised of D-amino acids is expected to have a greater retention of its biological activity in vivo.

The polypeptide can be prepared by any of a number of conventional techniques. The polypeptide can be isolated or purified from a naturally occurring source or from a recombinant source. Recombinant production is preferred. For instance, in the case of recombinant polypeptides, a DNA fragment encoding a desired peptide can be subcloned into an appropriate vector using well-known molecular genetic techniques (see, e.g., Maniatis et al., Molecular Cloning: A Laboratory Manual, 2nd ed. (Cold Spring Harbor Laboratory, 1982); Sambrook et al., Molecular Cloning A Laboratory Manual, 2nd ed. (Cold Spring Harbor Laboratory, 1989). The fragment can be transcribed and the polypeptide subsequently translated in vitro. Commercially available kits also can be employed (e.g., such as manufactured by Clontech, Palo Alto, Calif.; Amersham Pharmacia Biotech Inc., Piscataway, N.J.; InVitrogen, Carlsbad, Calif., and the like). The polymerase chain reaction optionally can be employed in the manipulation of nucleic acids.

The term "conservative substitution" as used herein, refers to the replacement of an amino acid present in the native sequence in the peptide or polypeptide with a naturally or non-naturally occurring amino acid or a peptidomimetic having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

Conservative amino acid substitution tables providing functionally similar amino acids are well known to one of ordinary skill in the art. The following six groups are examples of amino acids that may be considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

As naturally occurring amino acids are typically grouped according to their properties, conservative substitutions by naturally occurring amino acids can be determined bearing in mind the fact that replacement of charged amino acids by sterically similar non-charged amino acids are considered as conservative substitutions. For producing conservative substitutions by non-naturally occurring amino acids it is also possible to use amino acid analogs (synthetic amino acids) well known in the art. A peptidomimetic of the naturally occurring amino acid is well documented in the literature known to the skilled person and non-natural or unnatural amino acids are described further below. When affecting conservative substitutions the substituting amino acid should have the same or a similar functional group in the side chain as the original amino acid.

Alterations of the native amino acid sequence to produce mutant polypeptides, such as by insertion, deletion and/or substitution, can be done by a variety of means known to those skilled in the art. For instance, site-specific mutations can be introduced by ligating into an expression vector a synthesized oligonucleotide comprising the modified site. Alternately, oligonucleotide-directed site-specific mutagenesis procedures can be used, such as disclosed in Walder et al., Gene 42: 133 (1986); Bauer et al., Gene 37: 73 (1985); Craik, Biotechniques, 12-19 (January 1995); and U.S. Pat. Nos. 4,518,584 and 4,737,462. A preferred means for introducing mutations is the QuikChange Site-Directed Mutagenesis Kit (Stratagene, LaJolla, Calif.).

Any appropriate expression vector (e.g., as described in Pouwels et al., Cloning Vectors: A Laboratory Manual (Elsevier, N.Y.: 1985)) and corresponding suitable host can be employed for production of recombinant polypeptides of SMOC1, biologically active variants or analogs thereof. Expression hosts include, but are not limited to, bacterial species within the genera *Escherichia, Bacillus, Pseudomonas, Salmonella*, mammalian or insect host cell systems including baculovirus systems (e.g., as described by Luckow et al., Bio/Technology 6: 47 (1988)), and established cell lines such as the COS-7, C127, 3T3, CHO, HeLa, and BHK cell lines, and the like. The skilled person is aware that the choice of expression host has ramifications for the type of polypeptide produced. For instance, the glycosylation of polypeptides produced in yeast or mammalian cells (e.g., COS-7 cells) will differ from that of polypeptides produced in bacterial cells, such as *Escherichia coli*.

Alternately, a polypeptide of the invention, i.e. SMOC1, biologically active variants or analogs thereof, can be synthesized using standard peptide synthesizing techniques well-known to those of ordinary skill in the art (e.g., as summarized in Bodanszky, Principles of Peptide Synthesis (Springer-Verlag, Heidelberg: 1984)). In particular, the polypeptide can be synthesized using the procedure of solid-phase synthesis (see, e.g., Merrifield, J. Am. Chem. Soc. 85: 2149-54 (1963); Barany et al., Int. J. Peptide Protein Res. 30: 705-739 (1987); and U.S. Pat. No. 5,424,398). If desired, this can be done using an automated peptide synthesizer. Removal of the t-butyloxycarbonyl (t-BOC) or 9-fluorenyl-methyloxycarbonyl (Fmoc) amino acid blocking groups and separation of the polypeptide from the resin can be accomplished by, for example, acid treatment at reduced temperature. The polypeptide-containing mixture can then be extracted, for instance, with dimethyl ether, to remove non-peptidic organic compounds, and the synthesized polypeptide can be extracted from the resin powder (e.g., with about 25% w/v acetic acid). Following the synthesis of the polypeptide, further purification (e.g., using high performance liquid chromatography (HPLC)) optionally can be done in order to eliminate any incomplete polypeptides or free amino acids. Amino acid and/or HPLC analysis can be performed on the synthesized polypeptide to validate its identity. For other applications according to the invention, it may be preferable to produce the polypeptide as part of a larger fusion protein, such as by the methods described herein or other genetic means, or as part of a larger conjugate, such as through physical or chemical conjugation, as known to those of ordinary skill in the art and described herein.

A "peptidomimetic" is a synthetic chemical compound that has substantially the same structure and/or functional characteristics of a polypeptide of the invention, the latter being described further herein. Typically, a peptidomimetic has the same or similar structure as a polypeptide of the invention, for example the same or similar sequence of SEQ ID NO: 1 or SEQ ID NO: 3 that has the ability to promote blood glucose clearance. A peptidomimetic generally contains at least one residue that is not naturally synthesised. Non-natural components of peptidomimetic compounds may be according to one or more of: a) residue linkage groups other than the natural amide bond ('peptide bond') linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like.

Peptidomimetics can be synthesized using a variety of procedures and methodologies described in the scientific and patent literatures, e.g., Organic Syntheses Collective Volumes, Gilman et al. (Eds) John Wiley & Sons, Inc., NY, al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymot. 267: 220-234

SMOC1-Fusion Proteins

As used herein, the term "immunoglobulin heavy chain constant region" is used interchangeably with the terms "Fc", "Fc region" and "Fc domain" and is understood to mean the carboxyl-terminal portion of an immunoglobulin heavy chain constant region, or an analog or portion thereof capable of binding an Fc receptor. As is known, each immunoglobulin heavy chain constant region comprises four or five domains. The domains are named sequentially as follows: CH1-hinge-CH2-CH3(—CH4). CH4 is present in IgM, which has no hinge region. The immunoglobulin heavy chain constant region useful in the fusion proteins of the invention may comprise an immunoglobulin hinge region, a CH2 domain and a CH3 domain. As used herein, the term immunoglobulin "hinge region" is understood to mean an entire immunoglobulin hinge region or at least a portion of the immunoglobulin hinge region sufficient to form one or more disulfide bonds with a second immunoglobulin hinge region.

It is contemplated that suitable immunoglobulin heavy chain constant regions may be derived from antibodies belonging to each of the immunoglobulin classes referred to as IgA, IgD, IgE, IgG, and IgM, however, immunoglobulin heavy chain constant regions from the IgG class are preferred. Furthermore, it is contemplated that immunoglobulin heavy chain constant regions may be derived from any of the IgG antibody subclasses referred to in the art as IgG1, IgG2, IgG3, and IgG4. In one embodiment, an Fc region is derived from IgG1. In another embodiment, an Fc region is derived from IgG2.

Immunoglobulin heavy chain constant region domains have cross-homology among the immunoglobulin classes. For example, the CH2 domain of IgG is homologous to the CH2 domain of IgA and IgD, and to the CH3 domain of IgM and IgE. Preferred immunoglobulin heavy chain constant regions include protein domains corresponding to a CH2 region and a CH3 region of IgG, or functional portions or derivatives thereof. The choice of particular immunoglobulin heavy chain constant region sequences from certain immunoglobulin classes and subclasses to achieve a particular result is considered to be within the level of skill in the art. The Fc regions of the present invention may include the constant region such as, for example, an IgG-Fc, IgG-CH, an Fc or CH domain from another Ig class, i.e., IgM, IgA, IgE, IgD or a light chain constant domain. Truncations and amino acid variants or substitutions of these domains may also be included.

A variety of nucleic acid sequences encoding Fc fusion proteins may also be used to make the SMOC1-Fc fusion proteins of the invention. For example, the nucleic acid sequences may encode in a 5' to 3' direction, either the immunoglobulin heavy chain constant region and the SMOC1 polypeptide, or the SMOC1 polypeptide and the immunoglobulin heavy chain constant region. Furthermore, the nucleic acid sequences optionally may also include a "leader" or "signal" sequence based upon, for example, an immunoglobulin light chain sequence fused directly to a hinge region of the immunoglobulin heavy chain constant region. In a particular embodiment, when the Fc region is based upon IgG sequences, the Fc region encodes in a 5' to 3' direction, at least an immunoglobulin hinge region (i.e., a hinge region containing at least one cysteine amino acid capable of forming a disulfide bond with a second immunoglobulin hinge region sequence), an immunoglobulin CH2 domain and a CH3 domain. Furthermore, a nucleic acid sequence encoding the SMOC-1-Fc fusion proteins may also be integrated within a replicable expression vector that may express the Fc fusion protein in, for example, a host cell.

In one embodiment, the immunoglobulin heavy chain constant region component of the SMOC1-Fc fusion proteins is non-immunogenic or is weakly immunogenic in the subject. The Fc region is considered non- or weakly immunogenic if the immunoglobulin heavy chain constant region fails to generate a detectable antibody response directed against the immunoglobulin heavy chain constant region. Accordingly, the immunoglobulin heavy chain constant region should be derived from immunoglobulins present, or based on amino acid sequences corresponding to immunoglobulins present in the same species as the intended recipient of the fusion protein. In some embodiments, human immunoglobulin constant heavy region sequences are used for the SMOC1-Fc fusion protein, which is to be administered to a human. Nucleotide and amino acid sequences of human Fc IgG are known in the art and are disclosed, for example, in Ellison et al., Nucleic Acids Res. 10:4071-4079 (1982).

The SMOC1-Fc fusion proteins of the invention may be made using conventional methodologies known in the art. For example, SMOC1-Fc fusion constructs may be generated at the DNA level using recombinant DNA techniques, and the resulting DNAs integrated into expression vectors, and expressed to produce the SMOC1-Fc fusion proteins of the invention. As used herein, the term "vector" is understood to mean any nucleic acid comprising a nucleotide sequence competent to be incorporated into a host cell and to be recombined with and integrated into the host cell genome, or to replicate autonomously as an episome. Such vectors include linear nucleic acids, plasmids, phagemids, cosmids, RNA vectors, viral vectors and the like. Non-limiting examples of a viral vector include a retrovirus, an adenovirus and an adeno-associated virus. As used herein, the term "gene expression" or "expression" of a SMOC1-Fc fusion protein, is understood to mean the transcription of a DNA sequence, translation of the mRNA transcript, and secretion of an Fc fusion protein product. As an alternative to fusion of proteins by genetic engineering techniques, chemical conjugation using conventional chemical cross-linkers may be used to fuse protein moieties.

Sequences of constant regions useful for producing the proteins of the present invention, particularly SMOC1-Fc, may be obtained from a number of different sources. In some examples, the constant region or portion thereof of the protein is derived from a human antibody. The constant region or portion thereof may be derived from any antibody class, including IgM, IgG, IgD, IgA and IgE, and any antibody isotype, including IgG1, IgG2, IgG3 and IgG4. In one example, the constant region is human isotype IgG4 or a stabilized IgG4 constant region.

In one example, the Fc region of the constant region has a reduced ability to induce effector function, e.g., compared to a native or wild-type human IgG1 or IgG3 Fc region. In one example, the effector function is antibody-dependent cell-mediated cytotoxicity (ADCC) and/or antibody-dependent cell-mediated phagocytosis (ADCP) and/or complement-dependent cytotoxicity (CDC). Methods for assessing the level of effector function of an Fc region containing protein are known in the art and/or described herein.

In one example, the Fc region is an IgG4 Fc region (i.e., from an IgG4 constant region), e.g., a human IgG4 Fc region. Sequences of suitable IgG4 Fc regions will be apparent to the skilled person and/or available in publically available databases (e.g., available from National Center for Biotechnology Information).

In another example, the Fc region is a region modified to have reduced effector function, i.e., a "non-immunostimulatory Fc region". For example, the Fc region is an IgG1 Fc region comprising a substitution at one or more positions selected from the group consisting of 268, 309, 330 and 331. In another example, the Fc region is an IgG1 Fc region comprising one or more of the following changes E233P, L234V, L235A and deletion of G236 and/or one or more of the following changes A327G, A330S and P331S (Armour et al., Eur J Immunol. 29:2613-2624, 1999; Shields et al., J Biol Chem. 276(9):6591-604, 2001). Additional examples of non-immunostimulatory Fc regions are described, for example, in Dall'Acqua et al., J Immunol. 177: 1129-1138 2006; and/or Hezareh J Virol; 75: 12161-12168, 2001).

In another example, the Fc region is a chimeric Fc region, e.g., comprising at least one CH2 domain from an IgG4 antibody and at least one CH3 domain from an IgG1 antibody, wherein the Fc region comprises a substitution at one or more amino acid positions selected from the group consisting of 240, 262, 264, 266, 297, 299, 307, 309, 323, 399, 409 and 427 (EU numbering) (e.g., as described in WO2010/085682). Exemplary substitutions include 240F, 262L, 264T, 266F, 297Q, 299A, 299K, 307P, 309K, 309M, 309P, 323F, 399S, and 427F.

Compositions and Formulations.

Pharmaceutical compositions may be formulated for any appropriate route of administration including, for example, topical (for example, transdermal or ocular), oral, buccal, nasal, vaginal, rectal or parenteral administration. The term parenteral as used herein includes subcutaneous, intradermal, intravascular (for example, intravenous), intramuscular, spinal, intracranial, intrathecal, intraocular, periocular, intraorbital, intrasynovial and intraperitoneal injection, as well as any similar injection or infusion technique. In certain embodiments, compositions in a form suitable for oral use or parenteral use are preferred. Suitable oral forms include, for example, tablets, troches, lozenges, aqueous or oily suspensions, dispersible powders or granules, emulsions, hard or soft capsules, or syrups or elixirs. Within yet other embodiments, compositions provided herein may be formulated as a lyophilisate.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

Generally, a composition of this invention may be administered orally or parenterally (e.g., intravenous, intramuscular, subcutaneous or intramedullary), however, any other suitable route of administration is contemplated.

For buccal administration a composition of the invention may take the form of tablets or lozenges formulated in a conventional manner.

For purposes of transdermal (e.g., topical) administration, dilute sterile, aqueous or partially aqueous solutions (usually in about 0.1% to 5% concentration), otherwise similar to the above parenteral solutions, are prepared.

The various dosage units are each preferably provided as a discrete dosage tablet, capsules, lozenge, dragee, gum, or other type of solid formulation. Capsules may encapsulate a powder, liquid, or gel. The solid formulation may be swallowed, or may be of a suckable or chewable type (either frangible or gum-like). The present invention contemplates dosage unit retaining devices other than blister packs; for example, packages such as bottles, tubes, canisters, packets. The dosage units may further include conventional excipients well-known in pharmaceutical formulation practice, such as binding agents, gellants, fillers, tableting lubricants, disintegrants, surfactants, and colorants; and for suckable or chewable formulations.

Compositions intended for oral use may further comprise one or more components such as sweetening agents, flavouring agents, colouring agents and/or preserving agents in order to provide appealing and palatable preparations. Tablets contain the active ingredient in admixture with physiologically acceptable excipients that are suitable for the manufacture of tablets. Such excipients include, for example, inert diluents such as calcium carbonate, sodium carbonate, lactose, calcium phosphate or sodium phosphate, granulating and disintegrating agents such as corn starch or alginic acid, binding agents such as starch, gelatine or acacia, and lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatine capsules wherein the active ingredient is mixed with an inert solid diluent such as calcium carbonate, calcium phosphate or kaolin, or as soft gelatine capsules wherein the active ingredient is mixed with water or an oil medium such as peanut oil, liquid paraffin or olive oil.

Aqueous suspensions contain the active ingredient(s) in admixture with excipients suitable for the manufacture of aqueous suspensions. Such excipients include suspending agents such as sodium carboxymethylcellulose, methylcellulose, hydropropylmethylcellulose, sodium alginate, polyvinylpyrrolidone, gum tragacanth and gum acacia, and dispersing or wetting agents such as naturally-occurring phosphatides (for example, lecithin), condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol mono-oleate, or condensation products of ethylene oxide with partial esters derived from fatty acids and hexitol anhydrides such as polyethylene sorbitan monooleate. Aqueous suspensions may also comprise one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil such as arachis oil, olive oil, sesame oil or coconut oil, or in a mineral oil such as liquid paraffin. The oily suspensions may contain a thickening agent such as beeswax, hard paraffin or cetyl alcohol. Sweetening agents such as those set forth above, and/or flavouring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavouring and colouring agents, may also be present.

Pharmaceutical compositions may also be in the form of oil-in-water emulsions. The oily phase may be a vegetable oil such as olive oil or arachis oil, a mineral oil such as liquid paraffin, or a mixture thereof. Suitable emulsifying agents include naturally-occurring gums such as gum acacia or gum tragacanth, naturally-occurring phosphatides such as soy bean lecithin, and esters or partial esters derived from fatty acids and hexitol, anhydrides such as sorbitan monoleate, and condensation products of partial esters derived from fatty acids and hexitol with ethylene oxide such as polyoxyethylene sorbitan monooleate. An emulsion may also comprise one or more sweetening and/or flavouring agents.

Syrups and elixirs may be formulated with sweetening agents, such as glycerol, propylene glycol, sorbitol or sucrose. Such formulations may also comprise one or more demulcents, preservatives, flavouring agents and/or colouring agents.

A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatine-microcapsules, liposomes, albumin microspheres, microemulsions, nanoparticles or nanocapsules.

Preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerine, propylene glycol, and butylene glycol. Suitable emollients include lanolin alcohol, lanolin, lanolin derivatives, cholesterol, petrolatum, isostearyl neopentanoate and mineral oils. Suitable fragrances and colours include, but are not limited to, FD&C Red No. 40 and FD&C Yellow No. 5. Other suitable additional ingredients that may be included in a topical formulation include, but are not limited to, abrasives, absorbents, anticaking agents, antifoaming agents, antistatic agents, astringents (such as witch hazel), alcohol and herbal extracts such as chamomile extract, binders/excipients, buffering agents, chelating agents, film forming agents, conditioning agents, propellants, opacifying agents, pH adjusters and protectants.

A pharmaceutical composition may be formulated as inhaled formulations, including sprays, mists, or aerosols. For inhalation formulations, the composition or combination provided herein may be delivered via any inhalation methods known to a person skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent such as isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient.

Pharmaceutical compositions may also be prepared in the form of suppositories such as for rectal administration. Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release formulations such as a capsule that creates a slow release of modulator following administration. Such formulations may generally be prepared using well-known technology and administered by, for example, oral, rectal or subcutaneous implantation, or by implantation at the desired target site. Carriers for use within such formulations are biocompatible, and may also be biodegradable. Preferably, the formulation provides a relatively constant level of modulator release. The amount of modulator contained within a sustained release formulation depends upon, for example, the site of implantation, the rate and expected duration of release and the nature of the condition to be treated or prevented.

Kits

In another embodiment there is provided a kit or article of manufacture comprising SMOC1, a fusion protein or pharmaceutical composition as described herein.

In other embodiments there is provided a kit for use in a therapeutic or prophylactic application mentioned above, the kit including:
a container holding a therapeutic composition in the form of SMOC1 or a fusion protein as described herein, or pharmaceutical composition described herein;
a label or package insert with instructions for use.

In certain embodiments the kit may contain one or more further active principles or ingredients for treatment of a disease or disorder described herein.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a therapeutic composition which is effective for treating the condition and may have a sterile access port (for example the container may be an intravenous solution bag or a vial having a stopper pierceable by a hypodermic injection needle). The label or package insert indicates that the therapeutic composition is used for treating the condition of choice. In one embodiment, the label or package insert includes instructions for use and indicates that the therapeutic or prophylactic composition can be used to treat a disease described herein.

The kit may comprise (a) a therapeutic or prophylactic composition; and (b) a second container with a second active principle or ingredient contained therein. The kit in this embodiment of the invention may further comprise a package insert indicating the composition and other active principle can be used to treat a disorder or prevent a complication stemming from an impaired ability to clear glucose from the blood described herein. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments the therapeutic composition may be provided in the form of a device, disposable or reusable, including a receptacle for holding the therapeutic, prophylactic or pharmaceutical composition. In one embodiment, the device is a syringe. The device may hold 1-2 mL of the therapeutic composition. The therapeutic or prophylactic composition may be provided in the device in a state that is ready for use or in a state requiring mixing or addition of further components.

It will be understood, that the specific dose level for any particular patient will depend upon a variety of factors including the activity of the specific compound employed, the age, body weight, general health, sex, diet, time of administration, route of administration, and rate of excretion, drug combination (i.e. other drugs being used to treat the patient), and the severity of the particular disorder undergoing therapy.

SMOC1 as a Biomarker of Type 2 Diabetes

The present invention also provides a method for diagnosing an individual as having type 2 diabetes, or at risk of developing same, the method comprising:
 providing a test sample from an individual for whom a diagnosis of type 2 diabetes is to be determined;
 assessing the test sample for the level of SMOC1, thereby forming a test sample profile;
 providing a control profile containing data on the level of SMOC1 in peripheral blood of an individual without type 2 diabetes;
 comparing the test sample profile with the control profile to identify whether there is a difference in the level of SMOC1 as between the test sample profile and the control profile;
 determining that the individual has type 2 diabetes, or is at risk of developing the same, where the level of SMOC1 in the test sample profile is higher than the control profile;
 determining that the individual does not have type 2 diabetes, or is not at risk of developing the same, where the level of SMOC1 in the test sample profile is the same or lower than the control profile.

The present invention also provides a method for diagnosing an individual as having type 2 diabetes, or at risk of developing same, the method comprising:
 providing a test sample from an individual for whom a diagnosis of multiple type 2 diabetes is to be determined;
 assessing the test sample for the level of SMOC1, thereby forming a test sample profile;
 providing a control profile containing data on the level of SMOC1 in peripheral blood of an individual with type 2 diabetes;
 comparing the test sample profile with the control profile to identify whether there is a difference in the level of SMOC1 as between the test sample profile and the control profile;
 determining that the individual does not have type 2 diabetes, or is not at risk of developing the same, where the level of SMOC1 in the test sample profile is lower than the control profile;
 determining that the individual has type 2 diabetes, or is at risk of developing the same, where the level of SMOC1 in the test sample profile is the same or higher than the control profile.

Extraction and Assessment of SMOC1 Levels in the Test Sample

The test sample comprising SMOC1 can be any biological sample obtained from the individual, provided that SMOC1 can be measured from that sample. For example, in some embodiments, the sample can be a blood sample, from which the white blood cells, plasma or serum are then isolated. Alternatively, the sample could be a tissue biopsy, for example a biopsy of liver. Where the test sample is a tissue biopsy, the tissue may be fresh or fixed. In alternative embodiments, the test sample may be from an extracellular fluid such as saliva, tears, or sweat.

In one embodiment, whole blood can be collected into tubes containing EDTA, mixed by inversion several times, then centrifuged to separate plasma from the other blood constituents (for example, at 6,000×g for 5 min). The plasma can then be removed and stored for subsequent analysis and protein analysis.

In a particularly preferred embodiment, the sample is a sample of plasma or serum from an individual. The individual may be suspected of having type 2 diabetes, or be considered at risk of having type 2 diabetes. In certain embodiments, the individual may have previously been treated for type 2 diabetes, and the diagnostic methods described herein are performed for the purpose of assessing the success of that treatment (i.e., to determine if the individual still has type 2 diabetes).

Assessing the test sample for the level of SMOC1 may involve a direct measurement of the amount of SMOC1 in the test sample. Alternatively, the assessment may relate to reviewing data which includes SMOC1 levels that have been determined previously and is found in a central database. In some embodiments, a computer-based analysis program is used to translate the raw data generated by the detection assay (e.g., the level of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or stool sample) is obtained from a subject and submitted to a profiling service (e.g., clinical lab at a medical facility, genomic profiling business, etc.), to generate raw data.

The skilled person will be familiar with methods for extracting total protein from biological samples for the purposes of directly measuring the levels or amounts of specific proteins such as SMOC1. Such methods are described for example in Molecular Cloning: A Laboratory Manual, J. Sambrook et al., eds., 2nd edition, Cold Spring Harbor Laboratory Press, 1989, (incorporated herein by reference) or can be obtained using commercially available kits for the isolation of protein from biological samples.

The amount of SMOC1 (or concentration thereof) in the test sample and control profile can be quantified or measured by a variety of means that are well-known to those of skill in the art.

The present invention involves measuring in a sample of blood or other bodily fluid obtained from an individual, the amount of SMOC1 in the sample to facilitate a determination of whether the individual has, or is at risk of type 2 diabetes. For example, the method may comprise contacting a biopsy, including a sample of bodily fluid derived from the subject with a compound capable of binding to SMOC1, and detecting the formation of complex between the compound and SMOC1.

For the purposes of the diagnostic method described herein, the term 'SMOC1' includes fragments of SMOC1, including for example, immunogenic fragments and epitopes of SMOC1.

In one embodiment, the compound that binds SMOC1 is an antibody.

The term "antibody" as used herein includes intact molecules as well as molecules comprising or consisting of fragments thereof, such as, for example Fab, F(ab')2, Fv and scFv, as well as engineered variants including diabodies, triabodies, mini-bodies and single-domain antibodies which are capable of binding an epitopic determinant. Thus, antibodies may exist as intact immunoglobulins, or as modifications in a variety of forms.

In another embodiment, an antibody to SMOC1 is detected in a patient sample, wherein the amount of the antibody in the sample is informative in relation to whether the individual is at risk or has type 2 diabetes.

Preferred detection systems contemplated herein include any known assay for detecting proteins or antibodies in a biological test sample, such as, for example, SDS/PAGE, isoelectric focussing, 2-dimensional gel electrophoresis comprising SDS/PAGE and isoelectric focussing, an immunoassay, flow cytometry e.g. fluorescence-activated cell sorting (FACS), a detection based system using an antibody or non-antibody compound, such as, for example, a small molecule (e.g. a chemical compound, agonist, antagonist, allosteric modulator, competitive inhibitor, or non-competitive inhibitor, of the protein). In accordance with these embodiments, the antibody or small molecule may be used in any standard solid phase or solution phase assay format amenable to the detection of proteins. Optical or fluorescent detection, such as, for example, using mass spectrometry, MALDI-TOF, biosensor technology, evanescent fiber optics, or fluorescence resonance energy transfer, is clearly encompassed by the present invention. Assay systems suitable for use in high throughput screening of mass samples, e.g. a high throughput spectroscopy resonance method (e.g. MALDI-TOF, electrospray MS or nano-electrospray MS), are also contemplated.

Immunoassay formats are particularly suitable for detecting protein biomarkers such as SMOC1 in accordance with the method of the instant invention and include for example immunoblot, Western blot, dot blot, enzyme linked immunosorbent assay (ELISA), radioimmunoassay (RIA), enzyme immunoassay. Modified immunoassays utilizing fluorescence resonance energy transfer (FRET), isotope-coded affinity tags (ICAT), matrix-assisted laser desorption/ionization time of flight (MALDI-TOF), electrospray ionization (ESI), biosensor technology, evanescent fiber-optics technology or protein chip technology are also useful.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

In a preferred embodiment, the SMOC1 levels are measured in blood plasma samples using a commercially available ELISA kit purchased from Cusabio Biotech (Dunwoody Georgia 30338) (Cat No. CSB-EL021842HU).

Quantitative immuno-polymerase chain reaction (qIPCR) utilizes nucleic acid amplification techniques to increase signal generation in antibody-based immunoassays. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods. Exemplary methods for performing iPCR are described in Niemeyer et al., (2007) Nature Protocols, 2:1918-30

Multiplexing systems such as Proseek Proximity Extension Assay and Bioplex Multiplex Assay are examples of suitable platforms for conducting immunoassays for the purposes of determining the amounts of the protein biomarkers herein described.

As used herein 'level of SMOC1' refers to the concentration of SMOC1, or fragments thereof, in a sample of blood, including blood serum or plasma. The concentration of SMOC1 will typically be normalised against the total sample volume analysed for the individual or alternatively against a housekeeping protein (for example, the concentration or level of SMOC1 in the sample may be normalised against the amount of albumin in the sample).

In accordance with the present invention, it will be appreciated that it is not necessary for the full protein sequence of SMOC1 to be detected in the test sample. For example, in certain embodiments, only specific fragments or peptides derived from SMOC1 or corresponding to SMOC1 may be detected in the sample, and will be sufficient to enable the skilled person to perform the methods of the invention.

Prior to testing for the level of SMOC1, the sample of bodily fluid or blood may be subjected to pre-treatment. Pre-treatment may involve, for example, preparing plasma from blood, diluting viscous fluids, and the like. Such methods may involve filtration, distillation, separation, concentration, inactivation of interfering components, and the addition of reagents. The selection and pre-treatment of biological samples prior to testing is well known in the art. In some embodiments, the sample of bodily fluid is subjected to preliminary processing designed to isolate or enrich the sample for low abundance proteins.

The skilled person will be familiar with various methods for obtaining biological samples including blood samples for individuals. Further, the skilled person will be familiar with various methods for ensuring proper storage of samples to ensure that there is no appreciable degradation of the protein contents of the sample (for example, the use of vacutainer blood collection tubes containing EDTA, heparin, citrate or other additives to prevent clotting or preserve the quality of the blood sample. The skilled person will also be familiar with methods for extracting plasma and serum from samples of whole blood.

Control Profile containing Data on the Level of SMOC1 in Peripheral Blood of an Individual In order to determine whether the levels of SMOC1 in a sample from an individual are indicative or not of the individual having or being at risk of type 2 diabetes, it is necessary to compare the levels of SMOC1 in a sample from the individual with a control profile.

The control profile (which may also be referred to as a reference data set) will typically be in the form of data on the level of SMOC1 in peripheral blood from one or more individuals. The control profile may be in the form of data from one or more individuals who do not have type 2 diabetes. Alternatively, the control profile may be in the form of data from one or more individual who do have type 2 diabetes.

The control profiles or reference datasets used in accordance with the methods of the present invention are in the form of representative data from one or more individuals and will contain sufficient representative data to enable the skilled person to determine, with an appropriate degree of certainty, whether an individual is at risk of type 2 diabetes or has type 2 diabetes. In certain embodiments, the reference dataset contains reference data from at least 10 individuals. The skilled person will also appreciate the greater prospects of correctly selecting an individual for treatment, if the dataset contains reference data from a greater number of individuals. Accordingly, in further embodiments, the reference dataset contains reference data from 10 or more individuals, 25 or more, 50 or more, 100 or more, 200 or more, 400 or more, 600 or more, 800 or more, or 1000 or more individuals.

For the purposes of determining whether an individual is at risk of type 2 diabetes, or has type 2 diabetes, the level of SMOC1 in a test sample from the individual is compared with the amount of SMOC1 in a reference data set or control profile.

For the purposes of making a determination based on the amounts of SMOC1 in the test sample and relative amount of SMOC1 in the control profile or reference data set:

"lower than" means that the level of SMOC1 in the test sample is more than 10% less than the level of SMOC1 in the control profile(s);

"the same as" means a level that is no more than 10% more or less than the level of the measured SMOC1 in the control profile;

"greater than" or "higher than" means that the level of SMOC1 in the test sample is more than 10% greater than the level of SMOC1 in the control profile. In certain embodiments, the methods of the present invention include a comparison of the level of SMOC1 measured in a sample from individual for whom the risk determination is being made. In some embodiments, that comparison may arise from an examination of the normalised amounts of SMOC1 protein obtained for the individual, and direct visual comparison of the amount of SMOC1 listed in a reference data set, such as, for example, an Excel spreadsheet. However, the skilled person will also appreciate that the invention is not so limited, such that the amount of SMOC1 in the individual may be measured in the same experiment as the amounts of SMOC1 in the one or more individuals making up the reference dataset. For example, if the SMOC1 is measured using an ELISA experiment on a multi-well plate, samples for the individual and reference data set can be included within the same plate. The comparison step, in these circumstances, may relate to a comparison of the degree of fluorescence intensity resulting from the ELISA experiment.

In circumstances where the reference data set contains biomarker information from a large number of individuals, it will be appreciated that there may be a need for statistical analyses to accurately determine the significance of any similarity or differences, as the case may be, between the amount of biomarker in the test sample and the amount of biomarker in the reference data set. The skilled person will be familiar with the different statistical methods that can be used to facilitate such an analysis, for example, statistical tests based on mean (student's t-test and extensions), Bayesian and empirical Bayesian methods, nonparametric tests, analysis of variance (ANOVA and extensions), empirical Bayes/moderated t-tests and Partial Least Squares (PLS), logistic regression analysis, full or partial least square methods, cluster analysis, machine learning techniques or techniques to analyse "big data".

It will be understood that the invention disclosed and defined in this specification extends to all alternative combinations of two or more of the individual features mentioned or evident from the text or drawings. All of these different combinations constitute various alternative aspects of the invention.

It will be understood that these examples are intended to demonstrate these and other aspects of the invention and although the examples describe certain embodiments of the invention, it will be understood that the examples do not limit these embodiments to these things. Various changes can be made and equivalents can be substituted and modifications made without departing from the aspects and/or principles of the invention mentioned above. All such changes, equivalents and modifications are intended to be within the scope of the claims set forth herein.

EXAMPLES

Example 1

Animal Care and Maintenance

The Monash University School of Biomedical Science Animal Ethics Committee approved surgical and experimental procedures. Male C57BL/6 mice were purchased from Monash Animal Services. All mice were bred and housed under controlled temperature (22° C.) and lighting (12:12 h light-dark cycle), and were fed either a chow (Specialty Feeds Irradiated Rat and Mouse Pellets; 19.6% energy from protein, 4.6% fat, 4.8% crude fibre, 14.3 MJ/Kg energy; both C57BL/6 mice and db/db mice) or high fat diet (HFD—C57BL/6 mice) (Specialty Feeds SF03-002; 19.5% protein, 36% fat, 4.7% crude fibre, 22.8 MJ/kg energy) ad libitum.

Intraperitoneal Glucose Tolerance Test (IP-GTT)

An intraperitoneal glucose tolerance test in mice was performed in lean mice at 10 weeks of age (n=20), and in HFD mice at 14 weeks of age (n=10). Mice were injected i.p with either saline or human recombinant SMOC1 (1.63 mg/kg body mass) (Life Research) 2 h prior to the glucose tolerance test. Mice were fasted for 4 h and injected with 2 g/kg glucose (50% dextrose solution) in the intraperitoneal cavity. Blood glucose levels were analysed via tail bleeds before and at 15, 30, 45, 60 and 90 min post injection.

Oral Glucose Tolerance Test (OGTT)

An oral glucose tolerance test was performed in lean mice at 12 weeks (n=4) and 16 weeks (n=16) of age, in HFD mice at 17 weeks of age (n=8) and at 20 weeks of age (n=8), and in db/db mice at 10 weeks of age (n=14) and 18 weeks of age (n=3). All mice were fasted for 4 hours prior to the commencement of experiments.

HFD was given for 3 and 6 weeks prior to the OGTT respectively.

Mice were injected intraperitoneally with either saline or human recombinant SMOC1 (1.63 mg/kg body mass) (Life Research) 2 h prior to the OGTT. Mice were fasted for 4 h and gavaged with 50 μg glucose (25% dextrose solution).

Blood glucose levels were analysed via tail bleeds before and at 15, 30, 45, 60 and 90 min post injection.

Blood Measurements

During the OGTT at t=0, 5, 15, 30, and 60 min 150 µL of blood was taken for the measurement of insulin, C-peptide, and GLP-1. Blood was collected using Kimble Chase® 75 mm heparinised capillary tubes and then transferred into a 1.7 mL Eppendorf Tube® which contained 1.5 µL of DPP4 inhibitor and 1.5 µL of Protease Inhibitor Cocktail (Sigma-Aldrich, St. Louis, Mo.). These inhibitors were included to prevent the conversion of active GLP1 to non-active GLP1. Samples were centrifuged for three minutes at 8,000 rpm; plasma was then transferred into new 1.7 mL Eppendorf Tubes and immediately frozen in liquid nitrogen for subsequent analysis. The GLP-1 enzyme linked immunoassay (ELISA) kit (Eagle Biosciences) was used to quantify bioactive GLP-1 (7-36) in mouse plasma. The mouse C-peptide ELISA kit (Crystal Chem.) was used to determine C-peptide concentration in mouse plasma.

Western Blot Analysis

Mouse plasma was diluted 1/50 in water and mixed with equal amounts of 2× Laemmli buffer (Biorad). Samples were boiled for 5 minutes at 95° C., and 20 µl of sample was loaded into 7.5% Criterion precast stain-free gels (Bio-Rad Laboratories, NSW, Australia). The amount loaded corresponds to 0.833 µl of plasma. The samples were subjected to SDS-PAGE and transferred to PVDF membranes (Trans-Blot® Turbo™ Transfer System, Bio-Rad Laboratories, NSW, Australia). Membranes were blocked with 5% milk in TBST, washed 3 times for 5 min in TBST, and probed with a rabbit polyclonal antibody raised against SMOC1 (ATLAS antibodies; HPA00415) (dilution 1/1000 in TBST+5% BSA) for 1 h at room temperature on a rocker. After washing 3 times for 5 min in TBST, the membranes were probed with the appropriate secondary antibody (Anti-rabbit ECL IgG, NA9340V, GE Healthcare) (dilution 1/2000 in 5% milk in TBST), and bands were detected with enhanced chemiluminescence as per the manufacturer instructions (Clarity™ Western ECL Substrate, Bio-Rad Laboratories, NSW, Australia) using the ChemiDoc™ MP System (Bio-Rad Laboratories, NSW, Australia), and quantified by densitometry (ImageLab, Version 4.1, Bio-Rad, NSW, Australia). The immunoreactive signal was normalized to the density of the total protein loading for each sample, which was obtained by visualization of the stain-free blot image and quantified using ImageLab.

Hepatocyte Isolation

Mice were anaesthetized with 3% isofluorane (Isorrane Inhalation Anaesthetic, Baxter) and a 24 gauge catheter was inserted into the hepatic portal vein. The liver was perfused with 50 ml of Hanks Buffered Salt Solution (HBSS) maintained at 37° C. using a peristaltic pump (Pharmacia Biotech P-1). Thereafter, the liver was perfused with 50 ml of collagenase buffer containing Liberase™ Research Grade (50 µg/ml) (Roche). The inferior vena cava was severed upon commencing the perfusion to allow drainage of the perfusate. The liver was dissected upon completion of the perfusion, minced with scissors, filtered through a 70 µm filter and after three washes in Hanks buffer, the hepatocytes were resuspended in filtered M199 medium as described below. The purity of hepatocytes was established in preliminary experiments by fluorescence-activated cell sorting.

Cell Culture and In Vitro Experimental Design.

Isolated primary hepatocytes were plated into tissue culture dishes in filtered M199 medium supplemented with 10% FBS, 1% penicillin-streptomycin (Gibco), 100 nM insulin (Sigma), 400 nM dexamethasone (Sigma) and 1.5 nM EGF (BD Biosciences). After four hours, the media was replaced with the same medium and supplements and 10 nM insulin. The culture medium was changed after 24 h and hepatocytes were washed with PBS then incubated in EX-CELL® 325 Protein-Free CHO Serum-Free Medium (SAFC Biosciences). Conditioned media was collected after 24 h, centrifuged at 300×g and the media collected and stored at −80° C.

iTRAQ Sample Preparation and Data Acquisition.

2.5 mL of each conditioned media from mouse hepatocytes were buffer exchanged into 0.5 M triethylammonium bicarbonate, 0.02% (w/v) SDS by ultrafiltration at 3000 g using a Vivaspin 5000 MWCO device (Sartorius, Bohemia, N.Y.). Proteins were reduced with TCEP, alkylated with MMTS, digested with trypsin and labelled with iTRAQ 8-plex reagents following the manufacturer's instructions. The iTRAQ labeled samples (4 HFD, 4 vehicle control) were combined in equal ratios and fractionated by strong cation exchange chromatography to yield 12 fractions. Each fraction was dried, re-suspended in 0.1% trifluoroacetic acid, 2% acetonitrile and loaded onto a reversed-phase Captrap (Michrom Bioresources, CA). Following desalting, the trap was switched in-line with a 150 µm×10 cm, C18 3 µm 300 Å ProteCol column (SGE, Ringwood, Vic) and analysed by nanoLC ESI MS/MS using a 120 min gradient with a Top 10 data dependent acquisition strategy with a 5600 TripleTOF mass spectrometer (AB Sciex, Redwood City, Calif.).

Proteomic Data Analysis.

ProteinPilot v4.0 (AB Sciex) was used for iTRAQ data processing. The SwissProt 2010 *Mus musculus* database containing 32614 entries (fwd+rev) was searched. In the ProteinPilot parameter settings, the thorough search mode was used, the precursor ion mass tolerance was 0.05 Da, the product ion mass tolerance was 0.1 Da, Unused Prot Score was >1.3 (95% confidence, corresponding to 0.3% protein FDR) and bias correction was enabled. The protein iTRAQ ratios are the geometric means of corresponding peptide iTRAQ ratios, which require a minimum of 2 peptide spectrum matches. Differentially expressed proteins were determined by an unpaired two sample T-test ($p<0.05$).

Example 2

Figure 1:
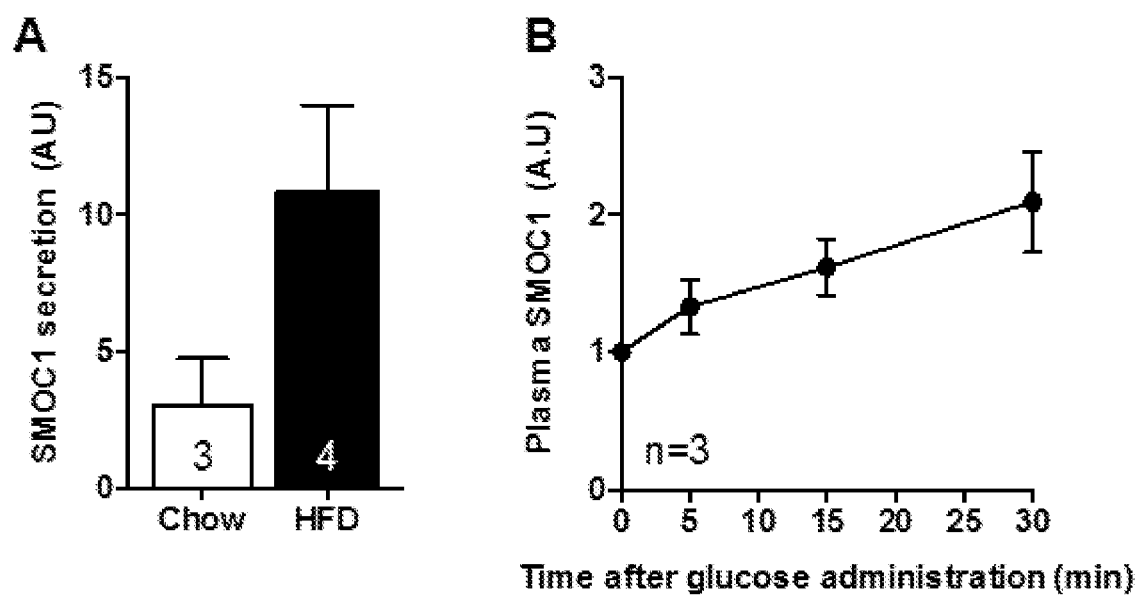
FIG. 1. SMOC1 is secreted by the liver and is induced by glucose administration in mice.

SMOC1 is secreted by the liver and is induced by glucose administration in mice (FIG. 1).

Male C57Bl/6J mice aged 12 weeks were fed a Chow diet or a high-fat diet (HFD) for 6 weeks (FIG. 1A). Hepatocytes were isolated and protein secretion from the liver was assessed by iTRAQ protein labelling and tandem mass spectrometry. Male C57Bl/6J mice were injected with glucose (2 g/kg body mass) and blood samples were obtained from a tail cut, the plasma collected after centrifugation and SMOC1 protein determined by immunoblot and normalized to protein loading (stain-free gel. N=3 mice) (FIG. 1B).

Example 3

SMOC1 accelerates or promotes plasma glucose clearance in both lean and high-fat diet (i.e. insulin resistant, pre-diabetic) mice in response to intraperitoneal glucose administration (FIG. 2).

Male C57Bl/6J mice aged 12 weeks and fed a Chow diet (Lean; FIG. 2A) or a high-fat diet (HFD; FIG. 2B). SMOC1 or control solution were injected 2 h prior to glucose administration. Blood samples were obtained before (0 min) and at 15 min intervals after glucose administration (2 g/kg body mass). Results from two independent experiments (Lean: n=9 Control, n=10 SMOC1, HFD: n=5 Control, n=5 SMOC1). Statistical analysis was performed by two-way repeated measures analysis of variance with Bonferroni post hoc testing. *p<0.05 vs corresponding time point between Control and SMOC1.

As shown in FIG. 2A, the administration of SMOC1 in lean mice resulted in a % decrease of blood glucose levels, compared to control, at 30, 60, 45 and 90 minutes of about 34%, about 41%, about 36% and about 25%, respectively.

As shown in FIG. 2B, the administration of SMOC1 in high-fat diet (i.e. insulin resistant, pre-diabetic) mice resulted in a % decrease of blood glucose levels, compared to control, at 30, 45, 60 and 90 minutes of about 3%, about 21%, about 38% and about 48%, respectively.

Example 4

SMOC1 accelerates or promotes plasma glucose clearance in lean mice in response to oral glucose administration (FIG. 3).

Male C57Bl/6J mice aged 12 weeks and fed a Chow diet (Lean). SMOC1 or control solution were injected 2 h prior to glucose administration. Blood samples were obtained before SMOC1 administration (−120 min), before glucose administration (0 min), and at 15 min intervals after glucose administration (50 µg glucose). FIG. 3A shows blood glucose, FIG. 3B shows plasma insulin and FIG. 3C shows plasma C-peptide levels. Results from two independent experiments (n=9 Control, n=10 SMOC1). Statistical analysis was performed by two-way repeated measures analysis of variance with Bonferroni post hoc testing. *P<0.05 vs corresponding time point between Control and SMOC1. Relevantly, there was no difference in fasting blood glucose levels between control and SMOC1 administered mice prior to oral glucose administration (i.e. between −120 min when SMOC1 administered and before time 0 when glucose was administered). This clearly shows that SMOC1 does not cause a reduction in the basal level of fasting blood glucose and does not induce hypoglycaemia. SMOC1 administration did not alter plasma insulin or C-peptide levels suggesting no effect on insulin secretion.

As shown in FIG. 3A, the administration of SMOC1 in lean mice resulted in a % decrease of blood glucose levels, compared to control, at 30, 45, 60 and 90 minutes of about 20%, about 24%, about 20% and about 16%, respectively.

Example 5

SMOC1 accelerates or promotes plasma glucose clearance in high-fat diet (i.e. insulin resistant, pre-diabetic) mice in response to oral glucose administration (FIG. 4).

Male C57Bl/6J mice aged 12 weeks and fed a high-fat diet (HFD). SMOC1 or control solution were injected 2 h prior to glucose administration. Blood samples were obtained before SMOC1 administration (−120 min), before glucose administration (0 min), and at 15 min intervals after glucose administration (50 µg glucose). FIG. 4A shows blood glucose, FIG. 4B shows plasma insulin and FIG. 4C shows plasma C-peptide levels. Results from two independent experiments (n=8 Control, n=7 SMOC1). Statistical analysis was performed by two-way repeated measures analysis of variance with Bonferroni post hoc testing. *P<0.05 vs corresponding time point between Control and SMOC1. Similarly to the results shown in FIG. 3, there was no difference in fasting blood glucose levels between control and SMOC1 administered mice prior to oral glucose administration (i.e. between −120 min when SMOC1 administered and before time 0 when glucose was administered). Again, this clearly shows that SMOC1 does not cause a reduction in the basal level of fasting blood glucose and does not induce hypoglycaemia. SMOC1 administration did not alter plasma insulin levels suggesting no effect on insulin secretion.

As shown in FIG. 4A, the administration of SMOC1 in high-fat diet (i.e. insulin resistant, pre-diabetic) mice resulted in a % decrease of blood glucose levels, compared to control, at 30, 45, 60 and 90 minutes of about 19%, about 26%, about 25% and about 26%, respectively.

Example 6

Effect of SMOC1, either in monomeric His tagged form, or dimeric Fc form, on plasma glucose responses to glucose administration (FIG. 5).

Male C57Bl/6J mice aged 15 weeks. SMOC1-his, SMOC1-fc or control solution were injected. Blood samples were obtained before SMOC1/control administration (−120 min), before glucose administration (0 min), and at 15 min intervals after glucose administration (2 g/kg body mass). FIG. 5A shows blood glucose 2 h after SMOC1/control injection, FIG. 5B shows blood glucose levels 24 h after SMOC1/control injection. Results from one experiment (n=3 per group). Statistical analysis was performed by two-way repeated measures analysis of variance with Bonferroni post hoc testing. *P<0.05 vs corresponding time point between Control and SMOC1-fc. Both SMOC1-his and SMOC1-fc significantly promoted blood glucose clearance immediately after glucose administration and also tended to do so 24 hours after glucose administration.

Example 7

SMOC1 is upregulated in individuals with type 2 diabetes compared with normoglycemic subjects (FIG. 6).

Plasma SMOC1 levels in obese humans without (normoglycemic, n=12) or with type 2 diabetes (T2D, n=11). *P=0.005 vs. normoglycemic.

An inability to efficiently clear glucose from the blood is a major defect of individuals with insulin resistance (pre-diabetes) and type 2 diabetes. The results from the experiments described herein demonstrate that SMOC1 can improve glucose clearance in lean, insulin sensitive mice and mice rendered overweight and insulin resistant (pre-diabetic) by high-fat feeding. SMOC1 is not inducing these beneficial effects by enhancing insulin secretion, rather, the data indicate that SMOC1 is acting as either (1) an insulin sensitizer or (2) a modulator of glucose clearance that works only when blood glucose levels are elevated (such as after a meal). This is clinically important as SMOC1 enhances glucose clearance without causing hypoglycaemia (low blood glucose), which is a problem with many existing diabetes medications.

Example 8

SMOC1 improves glucose tolerance in diabetic db/db mice (FIG. 7).

Female db/db mice aged 10 weeks were injected intraperitoneally with SMOC1 (3 mg/kg body mass) protein or control solution (0.9% saline) 2 h prior to glucose administration.

Blood samples were obtained before protein administration (−120 min), 2 h after protein administration (0 min) and at 15 min intervals after glucose administration (50 mg per mouse). FIG. 7A shows blood glucose over 90 minutes after glucose administration. Randomized cross over design with 5 days between trials. N=14 per group; Statistical analysis was performed by two-way repeated measured ANOVA. P=0.01 vs corresponding time point between control and SMOC1.

Example 9

An adeno-associated virus (AAV) encoding SMOC1 was obtained for the purpose of determining the effect of expressing SMOC1 in vivo (Vector Biolabs PA, USA, construct AAV8-ALB-hSMOC1-2A-GFP, product number AAV-223762). Briefly, the virus encoded AAV-8 capsid and AAV-2 ITR genes, human SMOC1 (the sequence provided in GeneBank Ref: BC011548.1), under the control of the albumin promoter, and upstream of a gene encoding eGFP. The construct included a region encoding a T2A linker for linking the SMOC1 and GFP proteins.

A construct encoding only GFP was used as a control (AAV8-AL.B-GFP, Vector Biolabs).

Female db/db mice aged 10 weeks were injected intravenously with the adenoassociated virus (AAV) containing cDNA encoding a SMOC1-GFP fusion, or with the control vector encoding GFP. Glucose tolerance was assessed as described in Example 8 at 18 weeks. FIG. 7B shows the blood glucose levels over 90 minutes after glucose administration. N=3 per group.

Statistical analysis was performed by two-way repeated measured ANOVA. P=0.001 vs corresponding time point between control and SMOC1.

Example 10

The skilled person will appreciate that varying doses of SMOC1 will be effective at decreasing blood glucose levels. depending on the level of severity of the insulin resistance in the individual being treated. The skilled person will be readily able to determine the appropriate dose of SMOC1 for promoting glucose clearance in an individual in need thereof.

It will be understood, however, that the specific dose level and frequency of dosage for any particular patient may be varied and will depend upon a variety of factors including the activity of the specific SMOC1 employed, the metabolic stability and length of action of that SMOC1, the age, body weight, general health, sex, diet, mode and time of administration, rate of excretion, drug combination, the severity of the particular condition, and the host undergoing therapy.

Moreover, the skilled person will be familiar with methods for determining an appropriate human dose based on the disclosure provided herein in relation to therapeutically effective doses for use in mice. For example, Human dose conversion can be by any of the relevant methods described in U.S. Department of Health and Human Services Food and Drug Administration Center for Drug Evaluation and Research (CDER), Estimating the Maximum Safe Starting Dose in Initial Clinical Trials for Therapeutics in Adult Healthy Volunteers. Rockville, Md. 2005, incorporated herein by reference.

The human equivalent doses described herein are derived using the methods described in the CDER 'Estimating the Maximum Safe Starting Dose in Initial Clinical Trials for Therapeutics in Adult Healthy Volunteers' for dose conversion based on body surface area. It will be appreciated that any variation on the methods described in the CDER document may also be utilised for determining an appropriate human dose from the dosages administered to mice, as described herein (for example, in some circumstances it may be appropriate to dose scaling based on body weight rather than on body surface area). Moreover, the skilled person will also be familiar with methods for determining the appropriate dose for a juvenile human (i.e., non-adult human), as well as methods for determining the appropriate dose in a non-human organism, to which the methods of the present invention may be applied. The skilled person will also be familiar with methods for adjusting the appropriate dose depending on the intended method of administration (for example, intravenous, intramuscular, subcutaneous, topical, oral or other method of administration).

Human Equivalent Dose (HED in mg/kg)=Animal Dose (mg/kg)×Animal K÷Human K, where K is a correction factor reflecting the relationship between body weight and body surface area.

For a typical adult (body weight 60 kg, body surface area 1.6 m$^2$), K is 37 and mouse K is 3. Thus, a 3 mg/kg dose described herein as being efficacious at reducing blood glucose levels in a model of type 2 diabetes with marked obesity, can be converted to about 0.25 mg/kg for an equivalent human dose.

A dose of SMOC1 of approximately 1.63 mg/kg body mass, demonstrated herein as being efficacious in decreasing blood glucose levels in both lean and high fat diet fed mice, can be converted to about 0.14 mg/kg for an equivalent human dose (assuming a typical adult human weight of 60 kg).

An adult suffering from type 2 diabetes, or obesity will likely weigh more than 60 kg and the skilled person will be familiar with appropriate methods for adjusting the dose of SMOC1 accordingly to account for the increased body surface area as compared with a 60 kg adult.

```
Human SMOC1 amino acid sequence
                                             SEQ ID NO: 1
M L P A R C A R L L T P H L L L V L V Q L S P

A R G H R T T G P R F L I S D R D P Q C N L H

C S R T Q P K P I C A S D G R S Y E S M C E Y

Q R A K C R D P T L G V V H R G R C K D A G Q

S K C R L E R A Q A L E Q A K K P Q E A V F V

P E C G E D G S F T Q V Q C H T Y T G Y C W C

V T P D G K P I S G S S V Q N K T P V C S G S

V T D K P L S Q G N S G R K D D G S K P P T M

L W I K H L V I K D S K L N N T N I R N S E K

V Y S C D Q E R Q S A L E E A Q Q N P R E G I

V I P E C A P G G L Y K P V Q C H Q S T G Y C

W C V L V D T G R P L P G T S T R Y V M P S C

E S D A R A K T T E A D D P F K D R E L P G C

P E G K K M E F I T S L L D A L T T D M V Q A

I N S A A P T G G G R F S E P D P S H T L E E

R V V H W Y F S Q L D S N S S N D I N K R E M

K P F K R Y V K K K A K P K K C A R R F T D Y
```

-continued
C D L N K D K V I S L P E L K G C L G V S K E
V G R L V

Human SMOC1 nucleotide sequence
SEQ ID NO: 2
ATGCTGCCCGCGCTGCGCCCGCCTGCTCACGCCCCACTTGCTGCTGGT
GTTGGTGCAGCTGTCCCCTGCTCGCGGCCACCGCACCACAGGCCCCAGGT
TTCTAATAAGTGACCGTGACCCACAATGCAACCTCCACTGCTCCAGGACT
CAACCCAAACCCATCTGTGCCTCTGATGGCAGGTCCTACGAGTCCATGTG
TGAGTACCAGCGAGCCAAGTGCCGAGACCCGACCCTGGGCGTGGTGCATC
GAGGTAGATGCAAAGATGCTGGCCAGAGCAAGTGTCGCCTGGAGCGGGCT
CAAGCCCTGGAGCAAGCCAAGAAGCCTCAGGAAGCTGTGTTTGTCCCAGA
GTGTGGCGAGGATGGCTCCTTTACCCAGGTGCAGTGCCATACTTACACTG
GGTACTGCTGGTGTGTCACCCCGGATGGGAAGCCCATCAGTGGCTCTTCT
GTGCAGAATAAAACTCCTGTATGTTCAGGTTCAGTCACCGACAAGCCCTT
GAGCCAGGGTAACTCAGGAAGGAAAGATGACGGGTCTAAGCCGACACCCA
CGATGGAGACCCAGCCGGTGTTCGATGGAGATGAAATCACAGCCCCAACT
CTATGGATTAAACACTTGGTGATCAAGGACTCCAAACTGAACAACACCAA
CATAAGAAATTCAGAGAAAGTCTATTCGTGTGACCAGGAGAGGCAGAGTG
CTCTGGAAGAGGCCCAGCAGAATCCCCGTGAGGGTATTGTCATCCCTGAA
TGTGCCCCTGGGGGACTCTATAAGCCAGTGCAATGCCACCAGTCCACTGG
CTACTGCTGGTGTGTGCTGGTGGACACAGGGCGCCCGCTGCCTGGGACCT
CCACACGCTACGTGATGCCCAGTTGTGAGAGCGACGCCAGGGCCAAGACT
ACAGAGGCGGATGACCCCTTCAAGGACAGGGAGCTACCAGGCTGTCCAGA
AGGGAAGAAAATGGAGTTTATCACCAGCCTACTGGATGCTCTCACCACTG
ACATGGTTCAGGCCATTAACTCAGCAGCGCCCACTGGAGGTGGGAGGTTC
TCAGAGCCAGACCCCAGCCACACCCTGGAGGAGCGGGTAGTGCACTGGTA
TTTTCAGCCAGCTGGACAGCAATAGCAGCAACGACATTAACAAGCGGGAGA
TGAAGCCCTTCAAGCGCTACGTGAAGAAGAAAGCCAAGCCCAAGAAATGT
GCCCGGCGTTTCACCGACTACTGTGACCTGAACAAAGACAAGGTCATTTC
ACTGCCTGAGCTGAAGGGCTGCCTGGGTGTTAGCAAAGAAGTAGGACGCC
TCGTCTAA SMOC1-Fc-3'His amino acid sequence
SEQ ID NO: 3
M L P A R C A R L L T P H L L L V L V Q L S P
A R G H R T T G P R F L I S D R D P Q C N L H
C S R T Q P K P I C A S D G R S Y E S M C E Y
Q R A K C R D P T L G V V H R G R C K D A G Q
S K C R L E R A Q A L E Q A K K P Q E A V F V
P E C G E D G S F T Q V Q C H T Y T G Y C W C
V T P D G K P I S G S S V Q N K T P V C S G S
V T D K P L S Q G N S G R K D D G S K P T P T
M E T Q P V F D G D E I T A P T L W I K H L V
I K D S K L N N T N I R N S E K V Y S C D Q E -continued
R Q S A L E E A Q Q N P R E G I V I P E C A P
G G L Y K P V Q C H Q S T G Y C W C V L V D T
G R P L P G T S T R Y V M P S C E S D A R A K
T T E A D D P F K D R E L P G C P E G K K M E
F I T S L L D A L T T D M V Q A I N S A A P T
G G G R F S E P D P S H T L E E R V V H W Y F
S Q L D S N S S N D I N K R E M K P F K R Y V
K K K A K P K K C A R R F T D Y C D L N K D K
V I S L P E L K G C L G V S K E V G R L V S H
H H H H H A S D K T H T C P P C P A P E L L G
G P S V F L P P K P K D T L M I S R T P E V
T C V V V D V S H E D P E V K F N W Y V D G V
E V H N A K T K P R E E Q Y N S T Y R V V S V
L T V L H Q D W L N G K E Y K C K V S N K A L
P A P I E K T I S K A K G Q P R E P Q V Y T L
P P S R E E M T K N Q V S L T C L V K G F Y P
S D I A V E W E S N G Q P E N N Y K T T P P V
L D S D G S F F L Y S K L T V D K S R W Q Q G
N V F S C S V M H E A L H N H Y T Q K S L S L
S P G SMOC1-Fc-3'His nucleotide sequence
SEQ ID NO: 4
ATGGGCTGGAGCCTGATCCTCCTGTTCCTCGTCGCTGTGGCTACAGGTAA
GGGGCTCACAGTAGCAGGCTTGAGGTCTGGACATATATATGGGTGACAAT
GACATCCACTTTGCCTTTCTCTCCACAGGTGGCGCGCATGCTGCCCGCGC
GCTGCGCCCGCCTGCTCACGCCCCACTTGCTGCTGGTGTTGGTGCAGCTG
TCCCCTGCTCGCGGCCACCGCACCACAGGCCCCAGGTTTCTAATAAGTGA
CCGTGACCCACAATGCAACCTCCACTGCTCCAGGACTCAACCCAAACCCA
TCTGTGCCTCTGATGGCAGGTCCTACGAGTCCATGTGTGAGTACCAGCGA
GCCAAGTGCCGAGACCCGACCCTGGGCGTGGTGCATCGAGGTAGATGCAA
AGATGCTGGCCAGAGCAAGTGTCGCCTGGAGCGGGCTCAAGCCCTGGAGC
AAGCCAAGAAGCCTCAGGAAGCTGTGTTTGTCCCAGAGTGTGGCGAGGAT
GGCTCCTTTACCCAGGTGCAGTGCCATACTTACACTGGGTACTGCTGGTG
TGTCACCCCGGATGGGAAGCCCATCAGTGGCTCTTCTGTGCAGAATAAAA
CTCCTGTATGTTCAGGTTCAGTCACCGACAAGCCCTTGAGCCAGGGTAAC
TCAGGAAGGAAAGATGACGGGTCTAAGCCGACACCCACGATGGAGACCCA
GCCGGTGTTCGATGGAGATGAAATCACAGCCCCAACTCTATGGATTAAAC
ACTTGGTGATCAAGGACTCCAAACTGAACAACACCAACATAAGAAATTCA
GAGAAAGTCTATTCGTGTGACCAGGAGAGGCAGAGTGCTCTGGAAGAGGC
CCAGCAGAATCCCCGTGAGGGTATTGTCATCCCTGAATGTGCCCCTGGGG
GACTCTATAAGCCAGTGCAATGCCACCAGTCCACTGGCTACTGCTGGTGT

```
GTGCTGGTGGACACAGGGCGCCCGCTGCCTGGGACCTCCACACGCTACGT
GATGCCCAGTTGTGAGAGCGACGCCAGGGCCAAGACTACAGAGGCGGATG
ACCCCTTCAAGGACAGGGAGCTACCAGGCTGTCCAGAAGGGAAGAAAATG
GAGTTTATCACCAGCCTACTGGATGCTCTCACCACTGACATGGTTCAGGC
CATTAACTCAGCAGCGCCCACTGGAGGTGGGAGGTTCTCAGAGCCAGACC
CCAGCCACACCCTGGAGGAGCGGGTAGTGCACTGGTATTTCAGCCAGCTG
GACAGCAATAGCAGCAACGACATTAACAAGCGGGAGATGAAGCCCTTCAA
GCGCTACGTGAAGAAGAAAGCCAAGCCCAAGAAATGTGCCCGGCGTTTCA
CCGACTACTGTGACCTGAACAAAGACAAGGTCATTTCACTGCCTGAGCTG
AAGGGCTGCCTGGGTGTTAGCAAAGAAGTAGGACGCCTCGTCTCACATCA
TCACCATCACCACGCTAGCGACAAAACTCACACATGCCCACCGTGCCCAG
CACCTGAACTCCTGGGGGGACCGTCAGTCTTCCTCTTCCCCCCAAAACCC
```

```
AAGGACACCCTCATGATCTCCCGGACCCCTGAGGTCACATGCGTGGTGGT
GGACGTGAGCCACGAAGACCCTGAGGTCAAGTTCAACTGGTACGTGGACG
GCGTGGAGGTGCATAATGCCAAGACAAAGCCGCGGGAGGAGCAGTACAAC
AGCACGTACCGTGTGGTCAGCGTCCTCACCGTCCTGCACCAGGACTGGCT
GAATGGCAAGGAGTACAAGTGCAAGGTCTCCAACAAAGCCCTCCCAGCCC
CCATCGAGAAAACCATCTCCAAAGCCAAAGGGCAGCCCCGAGAACCACAG
GTGTACACCCTGCCCCCATCCCGGGAGGAGATGACCAAGAACCAGGTCAG
CCTGACCTGCCTGGTCAAAGGCTTCTATCCCAGCGACATCGCCGTGGAGT
GGGAGAGCAATGGGCAGCCGGAGAACAACTACAAGACCACGCCTCCCGTG
CTGGACTCCGACGGCTCCTTCTTCCTCTATAGCAAGCTCACCGTGGACAA
GAGCAGGTGGCAGCAGGGGAACGTCTTCTCATGCTCCGTGATGCATGAGG
CTCTGCACAACCACTACACGCAGAAGAGCCTCTCCCTGTCCCCGGGTAA
```

The invention claimed is:

1. A method of increasing glycemic control in an individual, the method comprising administering SMOC1 or a fusion protein comprising SMOC1, to the individual prior to, or after an event that raises the blood glucose level in the individual, thereby increasing glycemic control in the individual.

2. A method of claim 1, wherein the method further comprises the step of:
   identifying an individual with impaired ability to clear glucose from the blood.

3. A method of claim 1, wherein the method is for treating or preventing a disorder arising from an increased blood glucose level in an individual, the method comprising administering SMOC1 or a fusion protein comprising SMOC1, thereby treating or preventing a disorder associated with increased blood glucose in the individual.

4. A method according to claim 3, wherein the disorder is insulin resistance.

5. A method according to claim 3, wherein the disorder is type 2 diabetes or pre-diabetes.

6. A method according to claim 1, wherein SMOC1 is administered orally.

7. A method according to claim 1, wherein SMOC1 is administered systemically.

8. A method according to claim 1, wherein the individual has an impaired ability to clear glucose from the blood.

9. A method according to claim 1, wherein the SMOC1 is human SMOC1.

10. A method according to claim 9, wherein human SMOC1 comprises or consists of an amino acid sequence shown in SEQ ID NO: 1.

11. A method according to claim 1, wherein the fusion protein comprising SMOC1 comprises a first amino acid sequence of SMOC1 and a second amino acid sequence of SMOC1.

12. A method of increasing glycemic control in an individual, the method comprising administering a fusion protein comprising SMOC1 to the individual, wherein the fusion protein comprising SMOC1 comprises an Fc portion of an antibody and a SMOC1 protein, thereby increasing glycemic control in the individual.

13. A method according to claim 12, wherein the fusion protein comprises the amino acid sequence shown in SEQ ID NO: 3.

14. A method of claim 12, wherein the method is for treating or preventing a disorder arising from an increased blood glucose level in an individual, the method comprising administering the fusion protein comprising SMOC1, thereby treating or preventing a disorder associated with increased blood glucose in the individual.

15. A method according to claim 14, wherein the disorder is insulin resistance.

16. A method according to claim 14, wherein the disorder is type 2 diabetes or pre-diabetes.

17. A method according to claim 12, wherein the SMOC1 fusion protein is administered orally.

18. A method according to claim 12, wherein the SMOC1 fusion protein is administered systemically.

19. A method according to claim 12, wherein the SMOC1 fusion protein is administered to the individual prior to an event that raises the blood glucose level in the individual.

20. A method according to claim 12, wherein the SMOC1 fusion protein is administered to the individual after an event that raises the blood glucose level in the individual.

21. A method according to claim 12, wherein the individual has an impaired ability to clear glucose from the blood.

22. A fusion protein comprising an amino acid sequence of SMOC1, wherein the fusion protein comprises the amino acid sequence shown in SEQ ID NO: 3.

23. A pharmaceutical composition for increasing glycemic control in an individual, the composition comprising a fusion protein comprising SMOC1 and a pharmaceutically acceptable diluent, excipient or carrier, wherein the fusion protein comprises the amino acid sequence shown in SEQ ID NO: 3.

* * * * *